United States Patent
Chao

(10) Patent No.: US 9,844,577 B1
(45) Date of Patent: Dec. 19, 2017

(54) MEDICINAL COMPOSITION FOR PREVENTION OR TREATMENT RETINAL ISCHEMIA

(71) Applicant: Hsiao-Ming Chao, Taipei (TW)

(72) Inventor: Hsiao-Ming Chao, Taipei (TW)

(73) Assignee: Fang-Ping Chao, Taipei (TW)

( * ) Notice: Subject to any disclaimer, the term of this patent is extended or adjusted under 35 U.S.C. 154(b) by 0 days.

(21) Appl. No.: 15/490,863

(22) Filed: Apr. 18, 2017

(51) Int. Cl.
*A61K 36/00* (2006.01)
*A61K 36/752* (2006.01)
*A61K 36/232* (2006.01)
*A61K 36/233* (2006.01)
*A61K 36/286* (2006.01)
*A61K 36/21* (2006.01)
*A61K 36/484* (2006.01)
*A61K 36/23* (2006.01)
*A61K 36/65* (2006.01)
*A61K 36/346* (2006.01)
*A61K 36/736* (2006.01)
*A61K 36/64* (2006.01)

(52) U.S. Cl.
CPC ............ *A61K 36/752* (2013.01); *A61K 36/21* (2013.01); *A61K 36/23* (2013.01); *A61K 36/232* (2013.01); *A61K 36/233* (2013.01); *A61K 36/286* (2013.01); *A61K 36/346* (2013.01); *A61K 36/484* (2013.01); *A61K 36/64* (2013.01); *A61K 36/65* (2013.01); *A61K 36/736* (2013.01)

(58) Field of Classification Search
None
See application file for complete search history.

(56) References Cited

PUBLICATIONS

Neville N. Osborne, Robert J. Casson, John P.M. Wood, Glyn Chidlow, Mark Graham, Jose Melena. Retinal ischemia: mechanisms of damage and potential therapeutic strategies. Progress in Retinal and Eye Research. 2004; 23(1):91-147.

Hsiao-Ming Chao, Ing-Ling Chen and Jorn-Hon Liu. S-allyl L-cysteine protects the retina against kainate excitotoxicity in the rat. The American Journal of Chinese Medicine. 2014; 42(3):693-708.

Pai-Huei Peng, Hsiao-Ming Chao, Shu-Hui Juan, Chau-Fong Chen, Jorn-Hon Liu and Mei-Lan Ko. Pharmacological preconditioning by low dose cobalt protoporphyrin induces heme oxygenase-1 overexpression and alleviates retinal ischemia-reperfusion injury in rats. Current Eye Research. 2011; 36(3):238-246.

Yan-Qing Chen, Wynn H.T. Pan, Jorn-Hon Liu, Mi-Mi Chen, Chi-Ming Liu, Ming-Yang Yeh, Shen-Kou Tsai, Mason Shing Young, Xiu-Mei Zhang and Hsiao-Ming Chao. The effects and underlying mechanisms of S-allyl I-cysteine treatment of the retina after ischemia/reperfusion. Journal of Ocular Pharmacology and Therapeutics. 28(2): 110-117, 2012.

Hsiao-Ming Chao, Min-Jay Chuang, Jorn-Hon Liu, Xiao-Qian Liu, Li-Kang Ho, Wynn H.T. Pan, Xiu-Mei Zhang, Chi-Ming Liu, Shen-Kou Tsai, Chi-Woon Kong, Shou-Dong Lee, Mi-Mi Chen, and Fang-Ping Chao. Baicalein protects against retinal ischemia by antioxidation, antiapoptosis, downregulation of HIF-1α, VEGF, and MMP-9 and upregulation of HO-1. Journal of Ocular Pharmacology and Therapeutics. 29(6): 539-549, 2013.

Jorn-Hon Liu, Hsiung Wann, Mi-Mi Chen, Wynn H.T. Pan, Yei-Ching Chen, Chi-Ming Liu, Ming-Yang Yeh, Shen-Kou Tsai, Mason Shing Young, Hui-Yen Chuang, Fang-Ping Chao, and Hsiao-Ming Chao. Baicalein significantly protects human retinal pigment epithelium cells against $H_2O_2$-induced oxidative stress by scavenging reactive oxygen species and downregulating the expression of matrix metalloproteinase-9 and vascular endothelial growth factor. Journal of Ocular Pharmacology and Therapeutics. 2010; 26(5):421-429.

*Primary Examiner* — Qiuwen Mi
(74) *Attorney, Agent, or Firm* — Hannah M. Tien

(57) ABSTRACT

This invention relates to a use of producing a medicinal composition for preventing or treating a disease, disorder or condition induced by retina ischemia, wherein the medicinal composition comprising 4.5 units by weight of *Radix Angelicae Sinensis* (Dang Gui), 4.5 units by weight of *Radix Rehmanniae glutinosae* (Di Huang), 3 units by weight of *Radix Paeoniae Rubra* (Chi Shao), from 2.25 to 2.3 units by weight of *Rhizoma Ligustici Chuanxiong* (Chuan Xiong), 6 units by weight of *Semen Pruni Persicae* (Táo Rén), 4.5 units by weight of *Flos Carthami Tinctorii* (Hong Hua), 1.5 units by weight of *Radix Glycyrrhizae Uralensis* (Gan Cao), 3 units by weight of *Fructus Aurantii* (Zhi Qiao), 1.5 units by weight of *Radix Bupleuri Chinense* (Chai Hu), 4.5 units by weight of *Radix Achyranthis Bidentatae* (Niu Xi), and from 2.25 to 2.3 units by weight of *Radix Platycodi Grandiflori* (Jie Geng).

6 Claims, 22 Drawing Sheets

SEQUENCE LISTING

```
<160> NUMBER OF SEQ ID NOS: 10

<210> SEQ ID NO 1
<211> LENGTH: 20
<212> TYPE: DNA
```

-continued

```
<213> ORGANISM: Artificial Sequence
<220> FEATURE:
<223> OTHER INFORMATION: Beta-actin forward primer for PCR
<220> FEATURE:
<221> NAME/KEY: misc_binding
<222> LOCATION: (1)..(20)

<400> SEQUENCE: 1
agggaaatcg tgcgtgacat                                                 20

<210> SEQ ID NO 2
<211> LENGTH: 20
<212> TYPE: DNA
<213> ORGANISM: Artificial Sequence
<220> FEATURE:
<223> OTHER INFORMATION: Beta-actin reverse primer for PCR
<220> FEATURE:
<221> NAME/KEY: misc_binding
<222> LOCATION: (1)..(20)

<400> SEQUENCE: 2
gaaccgctca ttgccgatag                                                 20

<210> SEQ ID NO 3
<211> LENGTH: 16
<212> TYPE: DNA
<213> ORGANISM: Artificial Sequence
<220> FEATURE:
<223> OTHER INFORMATION: VEGF forward primer for PCR
<220> FEATURE:
<221> NAME/KEY: misc_binding
<222> LOCATION: (1)..(16)

<400> SEQUENCE: 3
gcgggctgct gcaatg                                                     16

<210> SEQ ID NO 4
<211> LENGTH: 20
<212> TYPE: DNA
<213> ORGANISM: Artificial Sequence
<220> FEATURE:
<223> OTHER INFORMATION: VEGF reverse primer for PCR
<220> FEATURE:
<221> NAME/KEY: misc_binding
<222> LOCATION: (1)..(20)

<400> SEQUENCE: 4
tgcaacgcga gtctgtgttt                                                 20

<210> SEQ ID NO 5
<211> LENGTH: 20
<212> TYPE: DNA
<213> ORGANISM: Artificial Sequence
<220> FEATURE:
<223> OTHER INFORMATION: HIF-1alpha forward primer for PCR
<220> FEATURE:
<221> NAME/KEY: misc_binding
<222> LOCATION: (1)..(20)

<400> SEQUENCE: 5
acagctcccc agcatttcac                                                 20

<210> SEQ ID NO 6
<211> LENGTH: 22
<212> TYPE: DNA
<213> ORGANISM: Artificial Sequence
<220> FEATURE:
<223> OTHER INFORMATION: HIF-1alpha reverse primer for PCR
<220> FEATURE:
```

```
<221> NAME/KEY: misc_binding
<222> LOCATION: (1)..(22)

<400> SEQUENCE: 6
ggacaaactc cctcaccaaa aa                                              22

<210> SEQ ID NO 7
<211> LENGTH: 19
<212> TYPE: DNA
<213> ORGANISM: Artificial Sequence
<220> FEATURE:
<223> OTHER INFORMATION: PKM2 forward primer for PCR
<220> FEATURE:
<221> NAME/KEY: misc_binding
<222> LOCATION: (1)..(19)

<400> SEQUENCE: 7
tctacgtgga cgatgggct                                                  19

<210> SEQ ID NO 8
<211> LENGTH: 21
<212> TYPE: DNA
<213> ORGANISM: Artificial Sequence
<220> FEATURE:
<223> OTHER INFORMATION: PKM2 reverse primer for PCR
<220> FEATURE:
<221> NAME/KEY: misc_binding
<222> LOCATION: (1)..(21)

<400> SEQUENCE: 8
aggaagacct tctctgccgg a                                               21

<210> SEQ ID NO 9
<211> LENGTH: 20
<212> TYPE: DNA
<213> ORGANISM: Artificial Sequence
<220> FEATURE:
<223> OTHER INFORMATION: RBP2 forward primer for PCR
<220> FEATURE:
<221> NAME/KEY: misc_binding
<222> LOCATION: (1)..(20)

<400> SEQUENCE: 9
ttgtggtgac gtttcctcgt                                                 20

<210> SEQ ID NO 10
<211> LENGTH: 20
<212> TYPE: DNA
<213> ORGANISM: Artificial Sequence
<220> FEATURE:
<223> OTHER INFORMATION: RBP2 reverse primer for PCR
<220> FEATURE:
<221> NAME/KEY: misc_binding
<222> LOCATION: (1)..(20)

<400> SEQUENCE: 10
cagccagccc cacatctaag                                                 20
```

MEDICINAL COMPOSITION FOR PREVENTION OR TREATMENT RETINAL ISCHEMIA

This application contains a Sequence Listing in computer readable form. The computer readable form is incorporated herein by reference in its entirety.

FIELD OF THE INVENTION

This invention is related to a use of producing a medicinal composition for prevention or treatment of retinal ischemia.

BACKGROUND OF THE INVENTION

Central retinal artery occlusion (CRAO), central retinal vein occlusion (CRVO), branch retinal artery occlusion (BRAO), branch retinal vein occlusion (BRVO), glaucoma, and age-related macular degeneration (AMD) are all associated with retinal ischemia. All these diseases may lead to severe sequelae and therefore the management of retinal ischemia is crucial.

Neurons, such as retinal ganglion cells (RGCs) and amacrine cells, as well as their neuronal processes, which are located in the inner retina, are vulnerable to ischemia/reperfusion (I/R). After I/R, vimentin immunoreactivity has been shown to be increased in Müller cells. Ischemia induces angiogenesis. Furthermore, in the retina angiogenesis is often disorganized and typically results in edema and hemorrhage; these have adverse effects on visual functioning. There is an urgent need for therapies that promote endogenous protective responses and prevent harmful angiogenesis. Increased levels of the hypoxia-inducible factor-1α (HIF-1α) have been found to be present after retinal ischemia. HIF-1α binds to the hypoxia response elements of hypoxia-responsive target genes, and triggers the expression of the vascular endothelium growth factor (VEGF). It has been showed that an oxidative stress in the human retinal pigment epithelium results in up-regulation of VEGF. All the above evidence suggests that overexpression of HIF-1α and VEGF in the retina or in RGCs is directly related to an ischemic insult.

Anti-VEGF antibodies are world-wide clinically used but not completely effective for treating vision-threatening retinal disorders, namely proliferative diabetic retinopathy (PDR), wet age-related macular degeneration (wAMD) and central/branch retinal vein or artery occlusion. Moreover, patients administrated with anti-VEGF agents, even though vitreous/subretinal hemorrhage and macular edema were successfully dried, poor visual results have been presented.

Xue-Fu-Zhu-Yu decoction (XFZYD) is a famous traditional Chinese medicine formula for treating cardiovascular diseases for several centuries. It has been suggested that XFZYD potentiated recombinant tissue plasminogen activator (tPA)-mediated neuroprotection against ischemic stroke in rats. It has also been indicated that XFZYD could alleviate hypoxia and protect liver sinusoidal endothelial cell function by decreased VEGF and HIF-1α.

XFZYD composition comprises eleven components, namely *Radix Angelicae Sinensis* (Dang Gui), *Radix Rehmanniae glutinosae* (Di Huang), *Radix Paeoniae Rubra* (Chi Shao), *Rhizoma Ligustici Chuanxiong* (Chuan Xiong), *Semen Pruni Persicae* (Táo Rén), *Flos Carthami Tinctorii* (Hong Hua), *Radix Glycyrrhizae Uralensis* (Gan Cao), *Fructus Auranti* (Zhi Qiao), *Radix Bupleuri Chinense* (Chai Hu), *Radix Achyranthis Bidentatae* (Niu Xi), and *Radix Platycodi Grandiflori* (Jie Geng). From this composition, compounds with pharmaceutical functions were identified. Ferulic acid from Dang Gui and Chuan Xiong has been proved to scavenge hydroxyl radical and provide neuroprotection against retinal ischemia. Catalpol from Di Huang has significantly enhanced the activities of antioxidative enzymes, namely superoxide dismutase, glutathione peroxidase and catalase. Peoniflorinv from Chi Shao, amygdalin from Táo Rén, hydroxysafflor yellow A (HSYA) from Hong Hua, glycyrrhizin from Gan Cao, costunolide from Zhi Qiao and saikosaponin from Chai Hu can protect against brain ischemia or injury. Furthermore, amygdalin and HSYA had synergetic effects, such as decreasing plasma viscosity and platelet aggregation. Achyranthes bidentata polysaccharides from Niu Xi have an antioxidative potential. Aqueous extract from Jie Geng such as platycodins produced significant hepatoprotective effects by decreasing nitric oxide and lipid peroxidation in dose-dependent manners.

The work described herein is to investigate the use of XFZYD composition in attenuating retinal ischemic injury. Moreover, as PKM2 and RBP2 are co-activating HIF-1α that further triggers VEGF secretion and induces possible subsequent angiogenesis in the ischemic/hypoxic conditions, whether up-regulation of VEGF and HIF-1α coexists with PKM2 and RBP2, co-activators of HIF-1α, in the ischemic retina is also included in this work.

BRIEF SUMMARY OF THE INVENTION

A goal of this invention is to provide a use of producing a medicinal composition for preventing or treating a disease, disorder or condition induced by retina ischemia. The medicinal composition comprises Dang Gui, Di Huang, Chi Shao, Chuan Xiong, Táo Rén, Hong Hua, Gan Cao, Zhi Qiao, Chai Hu, Niu Xi, and Jie Geng.

DETAILED DESCRIPTION OF THE INVENTION

Figure 1A:
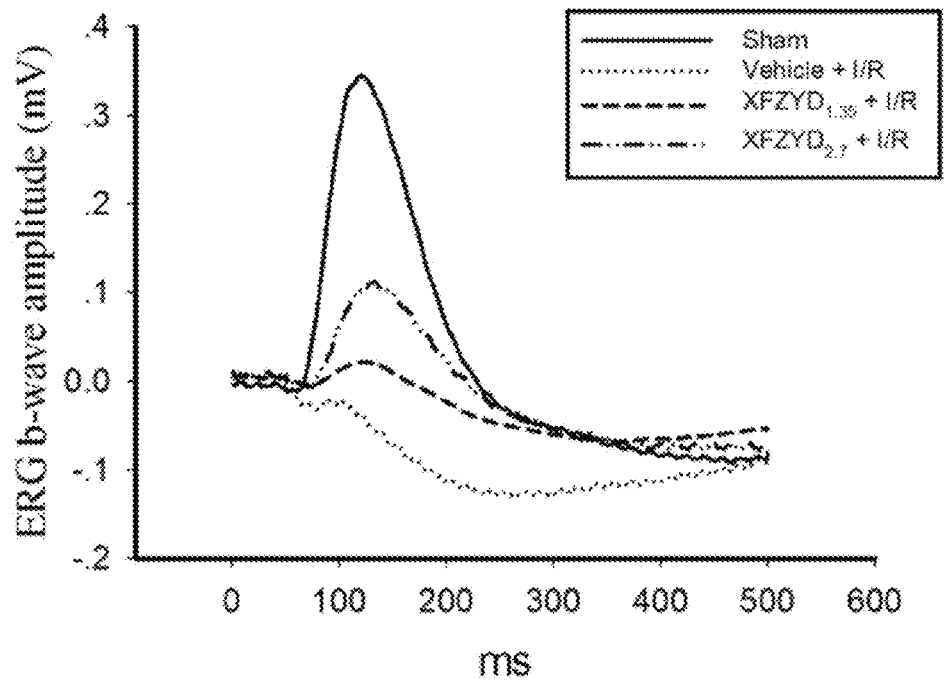
FIG. 1A is the electroretinogram (ERG) shows the effect of pre-ischemia administration or post-ischemia administration of XFZYD on retinal ischemia. When compared to the sham procedure retina (Sham), there was a considerable reduction in the b-wave amplitude following pressure-induced retinal ischemia plus reperfusion and preadministration (Vehicle+I/R) in a representative rat. This reduction was attenuated in a dose-dependent manner with preadministration (at 1.35 g/kg/day, $XFZYD_{1.35}$+I/R; at 2.7 g/kg/day, $XFZYD_{2.7}$+I/R) in one rat from each mentioned group. The results are expressed as mean±SD. XFZYD, Xue-Fu-Zhu-Yu decoction.
Figure 1B:
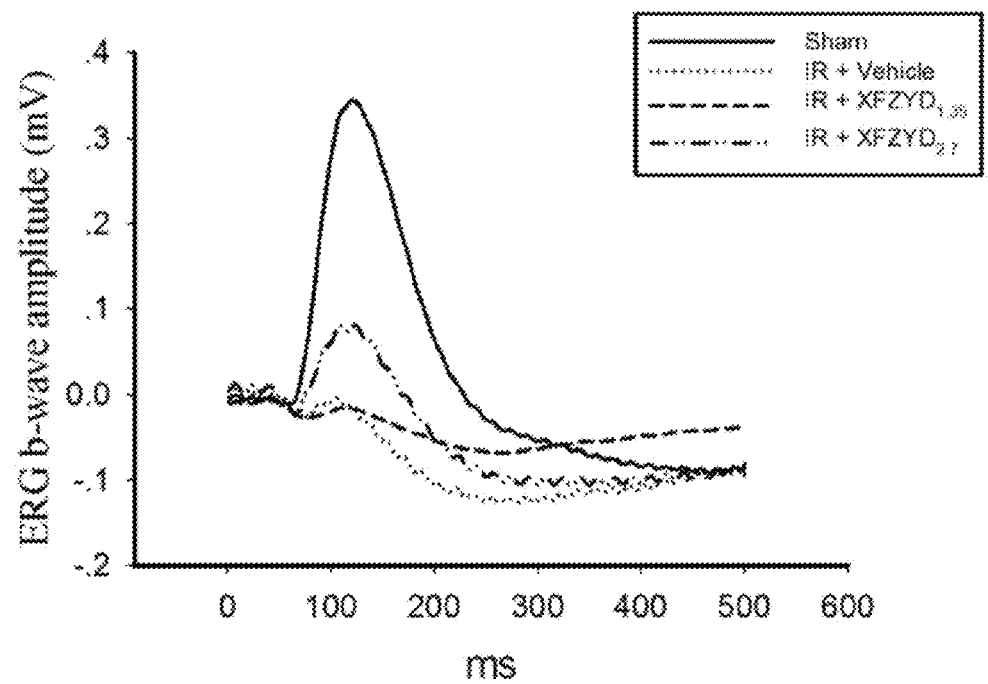
FIG. 1B is the electroretinogram (ERG) shows the effect of pre-ischemia administration or post-ischemia administration of XFZYD on retinal ischemia. When compared to the sham procedure retina (Sham), there was a considerable reduction in the b-wave amplitude following pressure-induced retinal ischemia plus reperfusion and postadministration of Vehicle (I/R+Vehicle) in a representative rat. This reduction was attenuated in a dose-dependent manner with postadministration of XFZYD (at 1.35 g/kg/day, I/R+$XFZYD_{1.35}$; at 2.7 g/kg/day, I/R+$XFZYD_{2.7}$) in one rat from each mentioned group. The results are expressed as mean±SD. XFZYD, Xue-Fu-Zhu-Yu decoction.

This work investigates effects of XFZYD to attenuate retinal ischemic injury. The effects were assessed by measuring changes in electroretinogram (ERG), density of RGCs, retinal thickness, choline acetyltransferase (ChAT) immunolabeled amacrine cells, and glial fibrillary acidic protein (GFAP)/Vimentin immunoreactivity that indexing Müller cells. mRNA and protein levels of VEGF, HIF-1α, PKM2 and RBP2 were analyzed by real-time polymerase chain reaction (PCR) and western blot, respectively.

In this work, retinal ischemic changes, namely a significant decrease in ERG b-wave amplitudes, a significant less numerous RGCs, a significant reduction in the inner/whole retinal thickness, a significant loss of the number of the ChAT immunolabeling amacrine cells as well as an obviously enhanced GFAP/Vimentin immunolabeling, and a significant upregulation of both the mRNA and protein levels of VEGF, HIF-1α, PKM2 and RBP2, have been found in the ischemic retina. Importantly, these ischemic detrimental effects were concentration-dependently and significantly altered when XFZYD was applied 7 consecutive days before or after retinal ischemia. In particular, the ischemia-associated VEGF, HIF-1α, PKM2 and RBP2 increases have been blunted by XFZYD.

In summary, this invention demonstrates that with pre-ischemia administration and post-ischemia administration of XFZYD mitigated the ischemia-induced reduction electrophysiologically, immunohistochemically, in terms of cell viability, and in terms of molecular biology.

This invention provides A use of producing a medicinal composition for preventing or treating a disease, disorder or condition induced by retina ischemia, wherein the composition comprising: 4.5 units by weight of Dang Gui, 1.5 units by weight of Chai Hu, 4.5 units by weight of Hong Hua, 3 units by weight of Zhi Qiao, 4.5 units by weight of Niu Xi, 1.5 units by weight of Gan Cao, from 2.25 to 2.3 units by weight of Chuan Xiong, 3 units by weight of Chi Shao, from 2.25 to 2.3 units by weight of Jie Geng, 6 units by weight of Táo Rén, and 4.5 units by weight of Di Huang. Preferably, wherein the Chuan Xiong is 2.3 units by weights, and the Jie Geng is 2.3 units by weight.

In one embodiment, wherein said composition is in a form selected from the group consisting of a solution, a dispersion in liquid phases, a suspension, an emulsion, a granulate, a powder, a capsule, a tablet, a pill, a pellet, or a solid mixture.

In one embodiment, wherein the disease, disorder or condition is central retinal artery occlusion (CRAO), central retinal vein occlusion (CRVO), branch retinal artery occlusion (BRAO), branch retinal vein occlusion (BRVO), glaucoma, proliferative diabetic retinopathy (DR) or age-related macular degeneration (AMD).

In one embodiment, wherein the preventing or treating retinal ischemia or retinal ischemia associated diseases is by downregulation of HIF-1α expression or VEGF secretion or both at the same time. Preferably, wherein the downregulation of HIF-1α expression or VEGF secretion or both at the same time is by inhibition of RBP2 or PKM2 or both at the same time.

Among the XFZYD composition, Dang Gui is prepared from a root of *Angelica sinensis* (Olive) Diels, Chai Hu is prepared form a whole plant or a root of *Bupleurum chinense* DC, Hong Hua is prepared form a flower of *Carthamus tinctorius* L, Zhi Qiao is prepared from an immature fruit of *Citrus aurantium* L. or *Sinensis Osbeck*, or a peel of a mature fruit of *Citrus aurantium* L. or *Sinensis Osbeck*, Niu Xi is prepared from a root of *Cyathula officinalis* Kuan or *Achyranthes bidentate* B1, Gan Cao is prepared from a root or a rhizome of *Glycyrrhiza glabra* L., *Glycyrrhiza uralensis* Fisch. or *Glycyrrhiza inflate* Bat, Chuan Xiong is prepared from a rhizome of *Ligusticum chuanxiong* Hort, Chi Shao is prepared from a root of *Paeonia lactiflora* Pall. or *Paeonia veitchii* Lynch, Jie Geng is prepared from a root of *Platycodon grandiflorum* (Jazq.) A. DC, Táo Rén is prepared from a seed of *Prunus Persica* (L) Batsch or *P. davidiana* (Carr.) Franch., Di Huang is prepared from a root of *Rehmannia glutinosa* Liboschitz.

The present invention also provides a use of a PKM2 inhibitor or a RBP2 inhibitor for preventing or treating a disease, disorder or condition induced by retina ischemia.

The compositions of the present invention can be used in the form of a solid, a solution, an emulsion, a dispersion, a micelle, a liposome, and the like, wherein the resulting composition contains one or more of the compounds of the present invention, as an active ingredient, in admixture with an organic or inorganic carrier or excipient suitable for enteral or parenteral applications. The active ingredient may be compounded, for example, With the usual non-toxic, pharmaceutically acceptable carriers for tablets, pellets, capsules, suppositories, solutions, emulsions, suspensions, and any other form suitable for use. The carriers which can be used include glucose, lactose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In additional auxiliary, stabilizing, thickening and coloring agents and perfumes may be used.

The compositions of the invention may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of a sweetening agent such as sucrose, lactose, or saccharin, flavoring agents such as peppermint, oil of Wintergreen or cherry, coloring agents and preserving agents in order to provide pharmaceutically elegant and palatable preparations. Tablets containing the active ingredient in admixture with non-toxic pharmaceutically acceptable excipients may also be manufactured by known methods. The excipients used may be, for example, (1) inert diluents such as calcium carbonate, lactose, calcium phosphate or sodium phosphate; (2) granulating and disintegrating agents such as corn starch, potato starch or alginic acid; (3) binding agents such as gum tragacanth, corn starch, gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,160,452; and 4,265,874, to form osmotic therapeutic tablets for controlled release.

In some cases, compositions for oral use may be in the form of hard gelatin capsules wherein the active ingredient is mixed with an inert solid diluent, for example, calcium carbonate, calcium phosphate or kaolin. They may also be in the form of soft gelatin capsules wherein the active ingredient is mixed with Water or an oil medium, for example, peanut oil, liquid paraffin, or olive oil.

Composition contemplated for use in the practice of the present invention may also be administered in the form of suppositories for rectal administration of the drug. These compositions may be prepared by mixing the drug with a suitable non-irritating excipient, such as cocoa butter, synthetic glyceride esters of polyethylene glycols, which are solid at ordinary temperatures, but liquify and/or dissolve in the rectal cavity to release the drug.

Since individual subjects may present a wide variation in severity of symptoms and each drug has its unique therapeutic characteristics, it is up to the practitioner to determine a subject's response to treatment and vary the dosages accordingly.

DESCRIPTION OF EMBODIMENTS

Examples

The examples below are non-limiting and are merely representative of various aspects and features of the present invention.

Example 1

The Effect of XFZYD on ERG b-Wave

Animals were treated according to the Association for Research in Vision and Ophthalmology Statement for the Use of Animals in Ophthalmology and Vision Research, and all the animal experiments were agreed by the Institutional Animal Care and Use Committee at Cheng Hsin General Hospital (CHGH; Taipei, Taiwan; Approval No: CHIACUC 104-05; Additional file 1). Six-week-old male Wistar rats (BioLasco, Taipei, Taiwan) were raised in a large plastic cage (Shineteh Instruments Co., Ltd., Taipei, Taiwan) of maximal 6 companions with the 40-60% humidity and at 19-23° C. The rats were arbitrarily allocated into one of the following groups: the animals (n=120) were used in various methods, namely ERG in 3 groups [(n=16): normal (n=5); I/R+Vehicle (n=5); I/R+XFZUD$_{1.35}$ (n=6)]; pathophysiology such as Cresyl Violet & ChAT labelling in 5 groups [(n=20): Sham, Vehicle+I/R, XFZUD$_{1.35}$+I/R, XFZUD$_{2.7}$+I/R, I/R+XFZYD$_{2.7}$ (n=4)]; fluorogold labelling, PCR and Western blot in 6 groups [(n=24): Normal, Sham, Vehicle+I/R, XFZUD$_{1.35}$+I/R, XFZUD$_{2.7}$ I/R, I/R+XFZYD$_{2.7}$ (n=4). Additionally, intravitreal injections of 5 µL of inhibitors were performed on ischemic eyes (n=12) 15 min before pressure-induced retinal ischemia in three other groups, namely I/R+Avastin (n=4), I/R+Shikonin (n=4) or I/R+JIB-04 (n=4). All rats were maintained on a 12-h light/dark period with 12-15 air exchanges/hour. The rats received food and water ad libitum. The animal studies were performed and summarized in Minimum Standards of Reporting Checklist.

Animal anesthesia was carried out using 100 mg/kg ketamine (Pfizer, NY, USA) and 5 mg/kg xylazine (Sigma-Aldrich, MO, USA), which were injected intraperitoneally given to the rats. Intraperitoneal injection of at least 140 mg/kg sodium pentobarbital (SCI Pharmtech, Taoyuan, Taiwan) was administered to sacrifice the rats utilizing a thoughtful way (Scientific Procedures Acts 1986).

After anesthesia, rats (200-250 g) were placed in a stereotaxic frame. A high intraocular pressure (HIOP) of 120 mmHg for 60 min was induced by cannulating the anterior chamber of one eye of an ischemic rat with a 30-gauge needle connected to an elevated 0.9% saline reservoir. The ischemic insult was confirmed by the detection of a pale eye fundus. In contrast, one eye of a control rat received a sham procedure where the saline reservoir was not elevated.

An intake of 1.35 or 2.7 g/kg/day XFZYD (Sun Ten Pharmaceutical CO, Taichung, Taiwan) was given for 7 consecutive days before or after HIOP induced retinal ischemia until the rats were sacrificed. The test rat whose eye was subjected to ischemia was fed with the constant volume (4 ml) of XFZYD or the equal volume of vehicle.

After anesthesia as described, pupil dilation with 1% tropicamide (Alcon, ZG, Switzerland) and 2.5% phenylephrine (Akorn, Inc., IL, USA) as well as surface anesthesia with 0.5% proparacaine (Alcon, ZG, Switzerland), a 30-gauge needle attached to a 25 μl syringe was used to perform intravitreal injections. In certain instances, intravitreal injections 5 μl of 4 μM Shikolin (Sigma-Aldrich, MO, USA), 10 μM JIB-04 (Sigma-Aldrich, MO, USA), 5 μl of 100 mg/4 ml Avastin (Hoffmann-La Roche, Basel, Switzerland) or of vehicle (an equal volume of dimethyl sulfoxide; J. T. Baker, NJ, USA) were performed on ischemic eyes fifteen minutes before pressure induced retinal ischemia.

Flash ERG recordings were performed on all the rats before retinal ischemia (day 0) as well as following 7 consecutive days of pre-ischemia or post-ischemia administration of XFZYD or vehicle. The rats were dark adapted for at least 8 hours, then they were anesthetized during the ERG recordings; for this, pupils were dilated with 1% tropicamide and 2.5% phenylephrine (Akorn, Inc., IL, USA) as well as ocular surfaces were anesthetized with 0.5% proparacaine (Alcon, ZG, Switzerland). A strobe was placed 2 cm in front of the rat eye to provide a stimulus of 0.5 Hz. Fifteen consecutive responses were recorded at 2-second intervals and at 10 kHz; the responses were amplified and averaged using an amplifier P511/regulated power supply 107/stimulator PS22 (Grass-Telefactor; AstroNova, QC, Canada). For comparative purposes, the b-wave ratio, namely, the b-wave amplitude of the treated ischemic eye when compared with that of the untreated contralateral normal eye, was calculated. (Neville N. Osborne, Robert J. Casson, John P. M. Wood, Glyn Chidlow, Mark Graham, Jose Melena. Retinal ischemia: mechanisms of damage and potential therapeutic strategies. *Progress in Retinal and Eye Research.* 2004; 23(1):91-147; Hsiao-Ming Chao, Ing-Ling Chen and Jorn-Hon Liu. S-allyl L-cysteine protects the retina against kainate excitotoxicity in the rat. *The American Journal of Chinese Medicine.* 2014; 42(3):693-708). The animals with the b-wave ratios above 125% & below 75% were excluded.

Figure 1C:
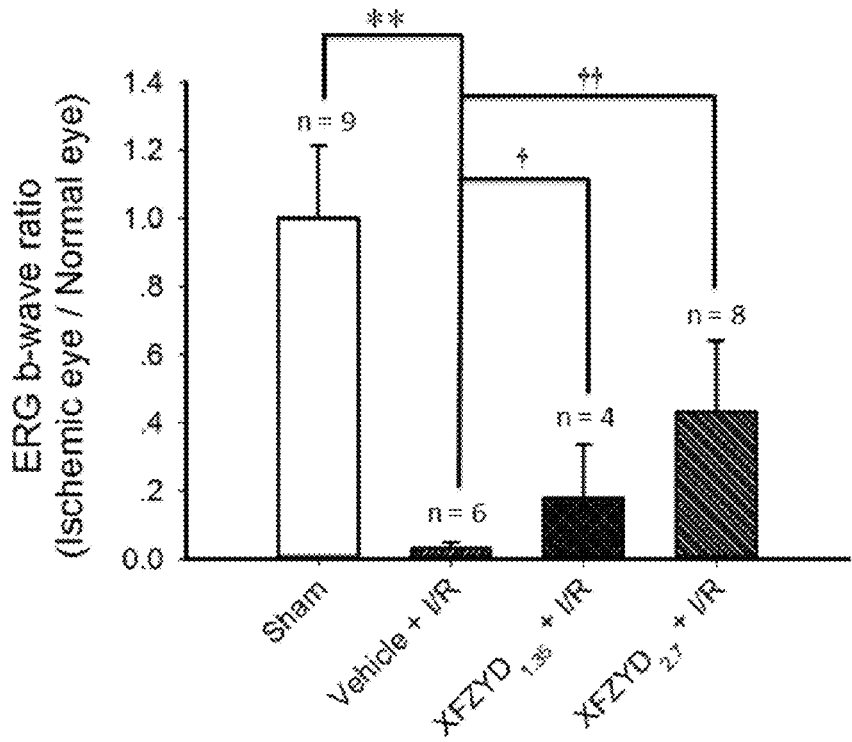
FIG. 1C is the electroretinogram (ERG) shows the effect of pre-ischemia administration or post-ischemia administration of XFZYD on retinal ischemia. In contrast with the sham procedure retina (Sham) group, there was a significantly (**, $p<0.01$) decreased b-wave ratio in the Vehicle+I/R following pressure-induced retinal ischemia. This ischemia-induced decrease was alleviated dose-dependently and significantly († , p<0.05; ††, p<0.01) with pre-ischemia administration of 1.35 and 2.7 g/Kg/day of XFZYD. The results are expressed as mean±SD. XFZYD, Xue-Fu-Zhu-Yu decoction.
Figure 1D:
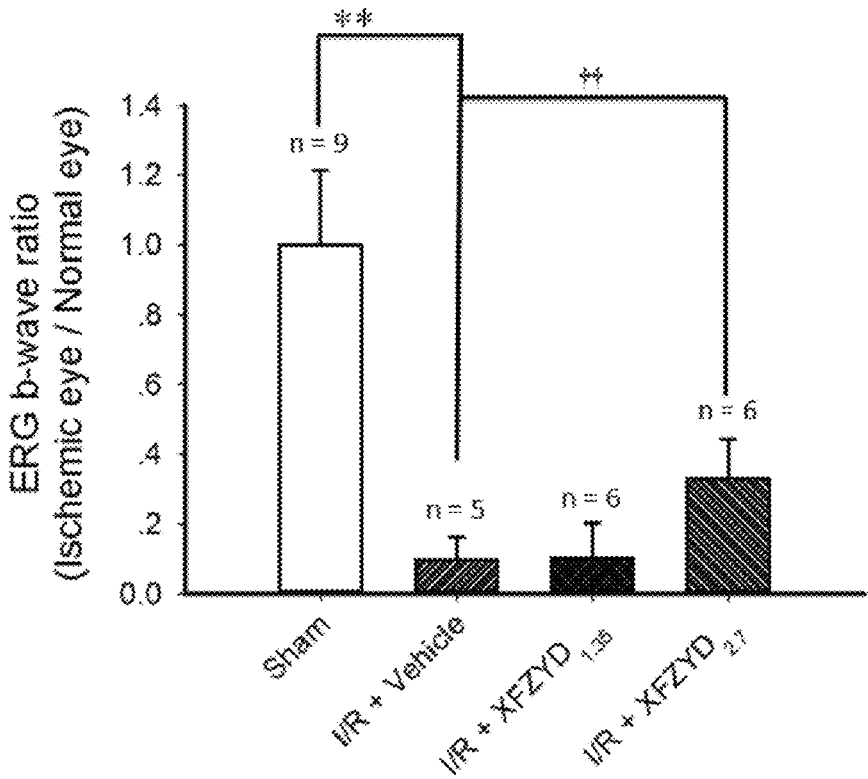
FIG. 1D is the electroretinogram (ERG) shows the effect of pre-ischemia administration or post-ischemia administration of XFZYD on retinal ischemia. In contrast with the sham procedure retina (Sham) group, there was a significantly (**, p<0.01) decreased b-wave ratio in the I/R+ Vehicle group following pressure-induced retinal ischemia. Post-ischemia administration of XFZYD at 2.7 g/Kg/day significantly (††, p<0.01) alleviated the reduction. The results are expressed as mean±SD. XFZYD, Xue-Fu-Zhu-Yu decoction.

The result is as shown in FIG. 1A-1D. In the retina subjected to the sham procedure (Sham, FIG. 1A, FIG. 1B), the ERG b-wave amplitude was calculated. After retinal ischemia plus reperfusion, the b-wave amplitude was considerably reduced. This reduction wasn't influenced with pre-ischemia administration or post-ischemia administration of vehicle (Vehicle+I/R: 0.01 mV, FIG. 1A; I/R+Vehicle: 0.02 mV, FIG. 1B). Nevertheless, pre-ischemia administration (XFZYD$_{1.35}$+I/R, 1.35 g/kg/day; XFZYD$_{2.7}$+I/R, 2.7 g/kg/day, FIG. 1A) and post-ischemia administration (I/R+XFZYD$_{1.35}$, 1.35 g/kg/day; I/R+XFZYD$_{2.7}$, 2.7 g/kg/day, FIG. 1B) of XFZYD mitigated the ischemia-induced reduction in b-wave and the values increased to 0.03, 0.13, 0.02 and 0.10 mV, respectively. As shown in FIG. 1C (n=4~9), in contrast with the sham group (1.00±0.21), there was a significant (p<0.001) reduction in the b-wave ratio in the Vehicle+I/R group (0.03±0.02). Of note, after pre-ischemia administration of XFZYD, there was a dose-response related (1.35 vs. 2.7 g/kg/day) and significant (at 1.35 g/kg/day, p=0.04; at 2.7 g/kg/day, p<0.001) mitigation in the ischemia-induced b-wave ratio reduction after ischemia plus reperfusion (XFZYD$_{1.35}$+I/R vs. XFZYD$_{2.7}$+I/R=0.18±0.16 vs. 0.43±0.21). Again, in FIG. 1D (n=5~9), in contrast with the sham group (1.00±0.21), there was also a significant (p<0.001) decrease in the b-wave ratio in the I/R+Vehicle group (0.10±0.07). Notably, after post-ischemia administration of XFZYD, there was dose-responsive (at 1.35 g/kg/day; 0.10±0.10; p=0.91) and significant (at 2.7 g/kg/day; 0.33±0.11; p=0.003) counteraction in the ischemia-induced b-wave ratio reduction. On the other hand, when the ERG b-wave ratios were compared, no significant (p=0.86) difference existed between the sham eye (n=9) and the normal eye (n=5; 1.02±0.16).

Example 2

The effect of XFZYD on the density of retrograde fluorogold labeled RGCs After anesthesia, the rats were made a 2-cm incision in the scalp, and drilled two small holes into the skull as described previously (Pai-Huei Peng, Hsiao-Ming Chao, Shu-Hui Juan, Chau-Fong Chen, Jorn-Hon Liu and Mei-Lan Ko. Pharmacological preconditioning by low dose cobalt protoporphyrin induces heme oxygenase-1 overexpression and alleviates retinal ischemia-reperfusion injury in rats. *Current Eye Research.* 2011; 36(3):238-246). Next, 2 μl of 5% fluorogold (Sigma-Aldrich, MO, USA) were injected by a micropipette at depths of 3.8, 4.0, and 4.2 mm below the skull. In all groups, the time of the fluorogold injection was performed three days before the rats were sacrificed. The retina was gently retrieved, fixated, dissected and processed as described previously (Pai-Huei Peng, Hsiao-Ming Chao, Shu-Hui Juan, Chau-Fong Chen, Jorn-Hon Liu and Mei-Lan Ko. Pharmacological preconditioning by low dose cobalt protoporphyrin induces heme oxygenase-1 overexpression and alleviates retinal ischemia-reperfusion injury in rats. *Current Eye Research.* 2011; 36(3):238-246). The average RGC density was defined as the ratio of the total RGC number to the total retinal area evaluated (Pai-Huei Peng, Hsiao-Ming Chao, Shu-Hui Juan, Chau-Fong Chen, Jorn-Hon Liu and Mei-Lan Ko. Pharmacological preconditioning by low dose cobalt protoporphyrin induces heme oxygenase-1 overexpression and alleviates retinal ischemia-reperfusion injury in rats. *Current Eye Research.* 2011; 36(3):238-246).

Figure 2A:
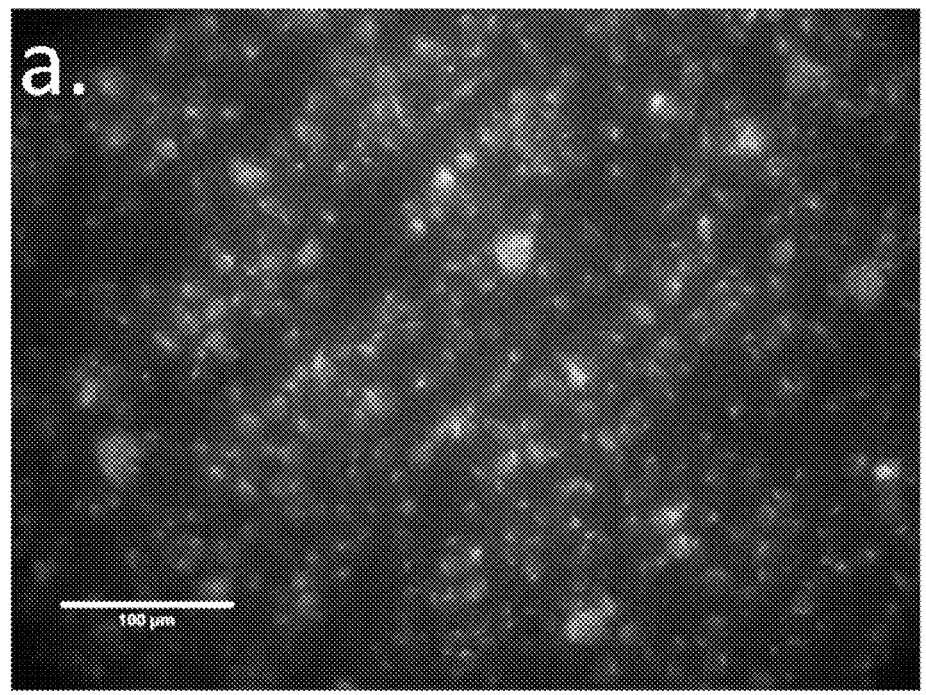
FIG. 2A shows the fluorogold labeling. The microscopic images demonstrate the density of retinal ganglion cells (RGCs) after the sham procedure (Sham). Scale bars=100 μm.
Figure 2B:
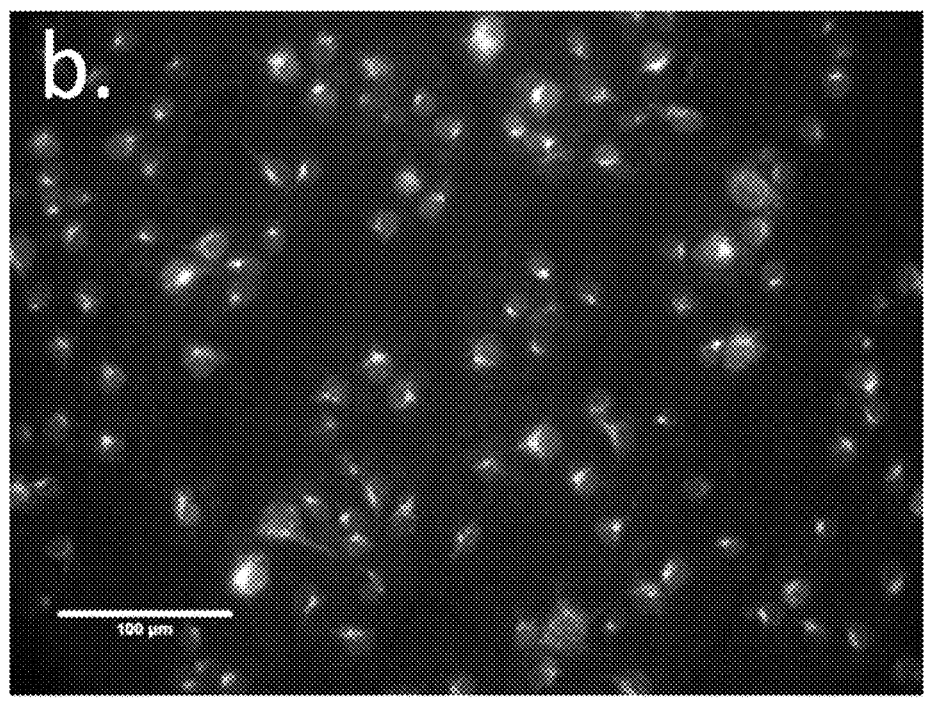
FIG. 2B shows the fluorogold labeling. The microscopic images demonstrate the density of retinal ganglion cells (RGCs) after the ischemia plus reperfusion (I/R) with pre-administered vehicle (Vehicle+I/R). Scale bars=100 μm.
Figure 2C:
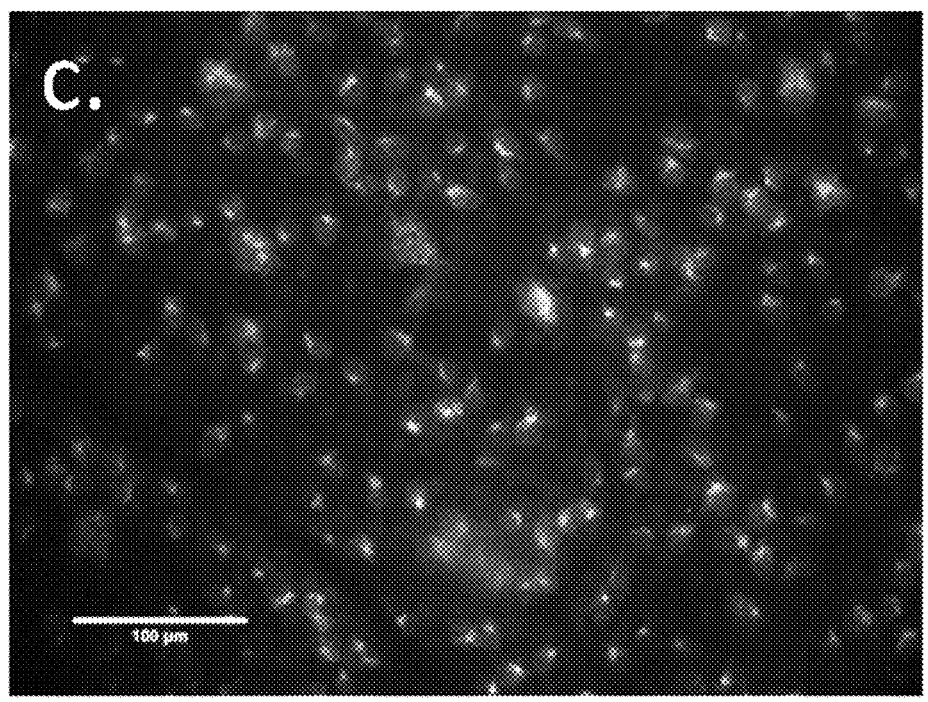
FIG. 2C shows the fluorogold labeling. The microscopic images demonstrate the density of retinal ganglion cells (RGCs) after the ischemia plus reperfusion (I/R) with pre-administered XFZYD at 1.35 g/kg/day (XFZYD$_{1.35}$+I/R). XFZYD, Xue-Fu-Zhu-Yu decoction. Scale bars=100 μm.
Figure 2D:
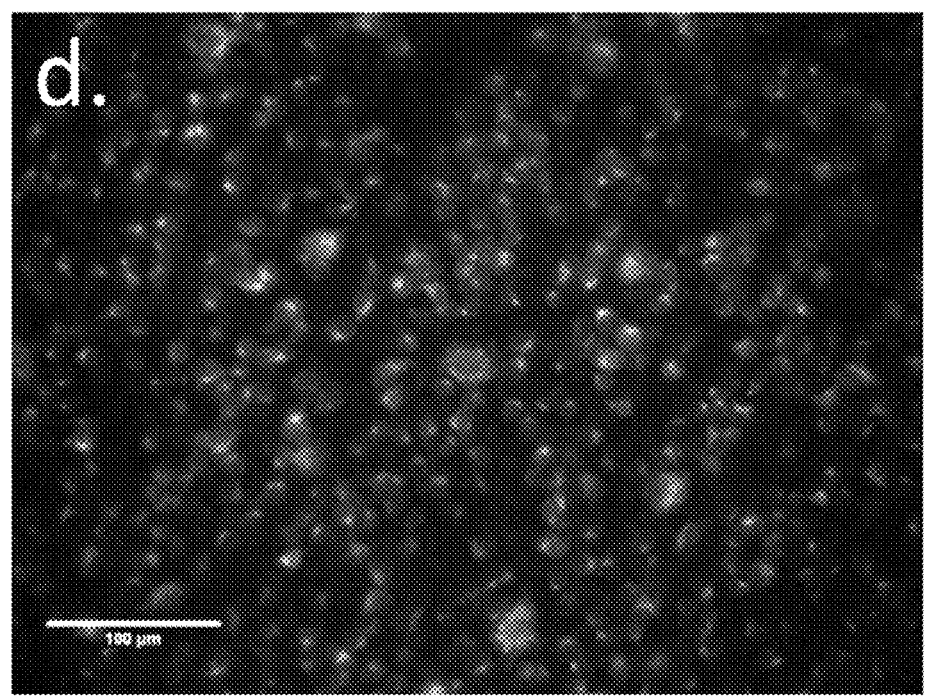
FIG. 2D shows the fluorogold labeling. The microscopic images demonstrate the density of retinal ganglion cells (RGCs) after the ischemia plus reperfusion (I/R) with pre-administered XFZYD at 2.7 g/kg/day (XFZYD$_{2.7}$+I/R). XFZYD, Xue-Fu-Zhu-Yu decoction. Scale bars=100 μm.
Figure 2E:
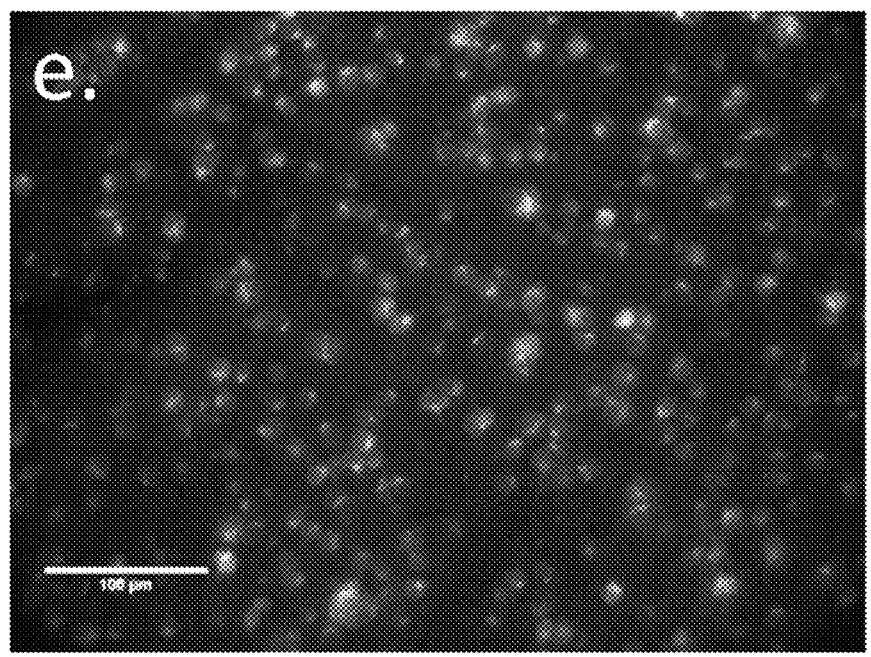
FIG. 2E shows the fluorogold labeling. The microscopic images demonstrate the density of retinal ganglion cells (RGCs) after the ischemia plus reperfusion (I/R) with post-administered XFZYD at 2.7 g/kg/day (I/R+XFZYD$_{2.7}$). XFZYD, Xue-Fu-Zhu-Yu decoction. Scale bars=100 μm.
Figure 2F:
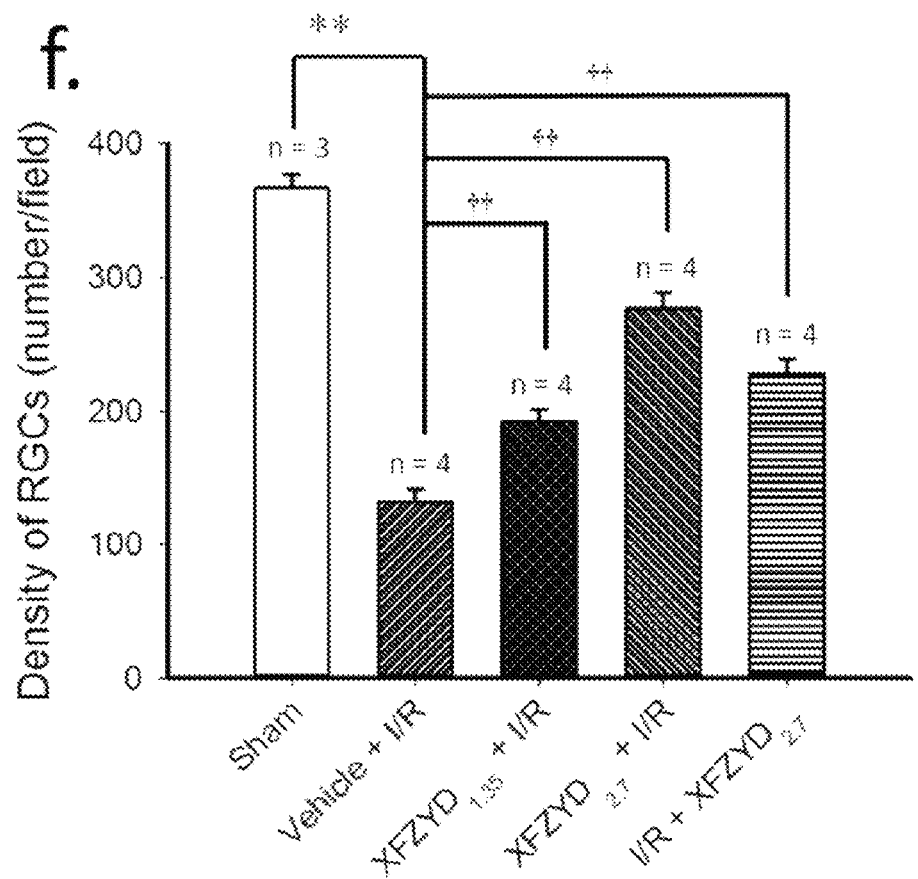
FIG. 2F shows the quantitative analysis of the density of RGCs in FIG. 2A, FIG. 2B, FIG. 2C, FIG. 2D and FIG. 2E. Each bar indicates the mean±SD (n=3~4). ** indicates significant difference (p<0.01; Sham vs. Vehicle+I/R); †† indicates significant difference (p<0.01; Vehicle+I/R vs. XFZYD$_{1.35}$+I/R, XFZYD$_{2.7}$+I/R or I/R+XFZYD$_{2.7}$). XFZYD, Xue-Fu-Zhu-Yu decoction.
Figure 3A:
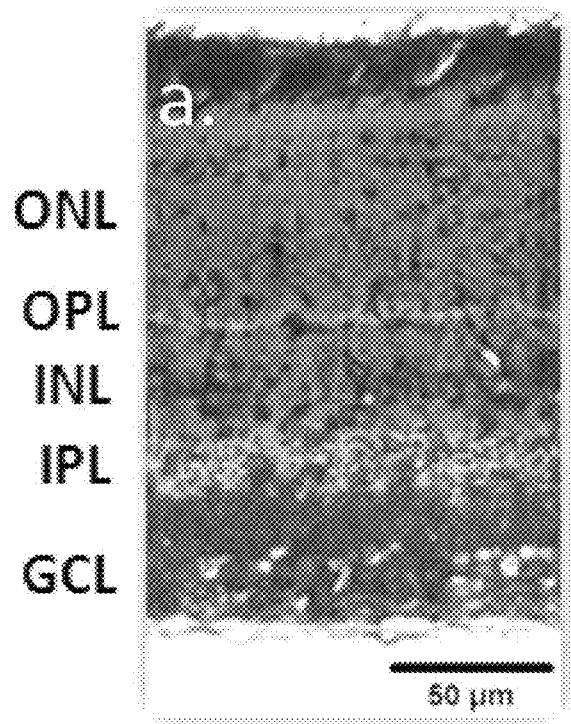
FIG. 3A shows the Cresyl Violet staining: analysis of the thickness of various retinal layers. This figure shows the section of the retina subjected to the sham procedure (Sham). Abbreviations: ONL, outer nuclear layer; OPL, outer plexiform layer; INL, inner nuclear layer; IPL, inner plexiform layer; GCL, ganglion cell layer. Scale bar=50 μm.
Figure 3B:
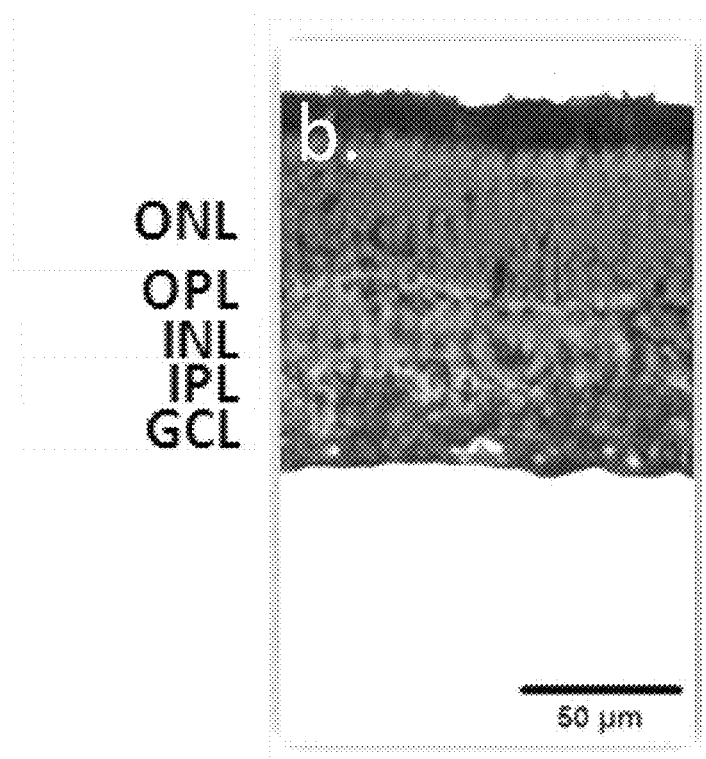
FIG. 3B shows the Cresyl Violet staining: analysis of the thickness of various retinal layers. This figure shows the section of the retina that received ischemia plus reperfusion (I/R) and preadministration of vehicle. Abbreviations: ONL, outer nuclear layer; OPL, outer plexiform layer; INL, inner nuclear layer; IPL, inner plexiform layer; GCL, ganglion cell layer. Scale bar=50 μm.
Figure 3C:
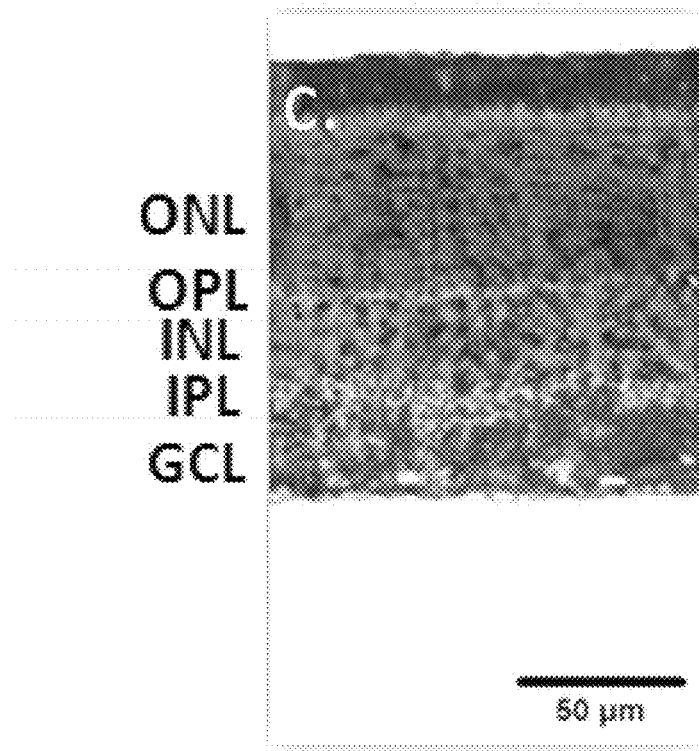
FIG. 3C shows the Cresyl Violet staining: analysis of the thickness of various retinal layers. This figure shows the section of the retina that received ischemia plus reperfusion and preadministration of 1.35 g/kg/day of XFZYD (XFZYD$_{1.35}$ I/R). Abbreviations: ONL, outer nuclear layer; OPL, outer plexiform layer; INL, inner nuclear layer; IPL, inner plexiform layer; GCL, ganglion cell layer. Scale bar=50 μm.
Figure 3D:
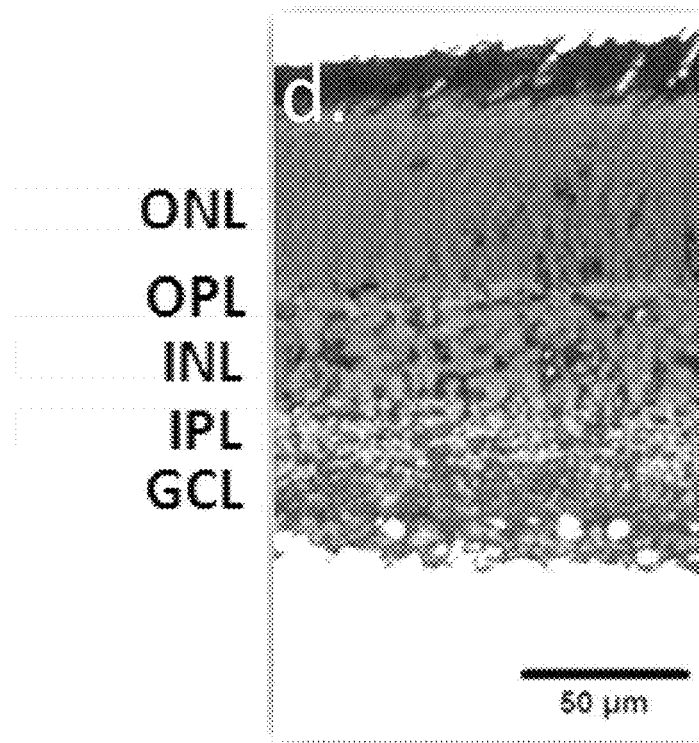
FIG. 3D shows the Cresyl Violet staining: analysis of the thickness of various retinal layers. This figure shows the section of the retina that received ischemia plus reperfusion and preadministration of 2.7 g/kg/day of XFZYD (XFZYD$_{2.7}$+I/R). Abbreviations: ONL, outer nuclear layer; OPL, outer plexiform layer; INL, inner nuclear layer; IPL, inner plexiform layer; GCL, ganglion cell layer. Scale bar=50 μm.
Figure 3E:
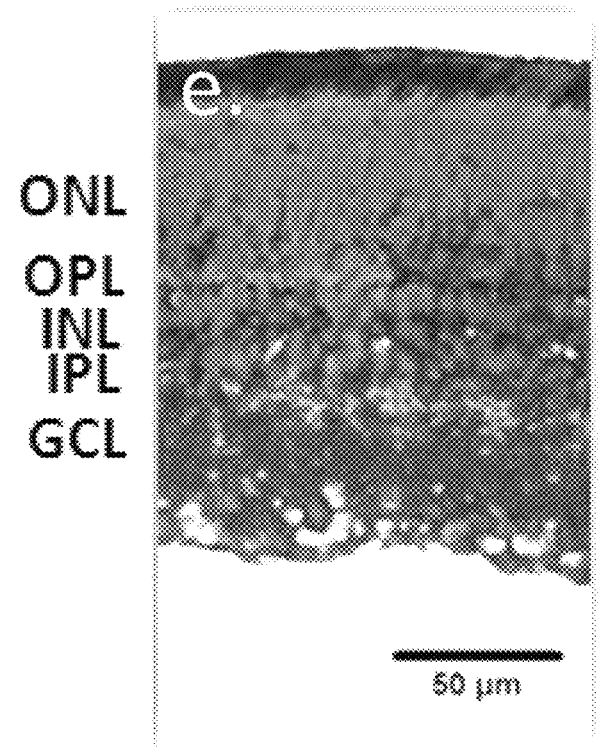
FIG. 3E shows the Cresyl Violet staining: analysis of the thickness of various retinal layers. This figure shows the section of the retina that received ischemia plus reperfusion and postadministration with 2.7 g/kg/day of XFZYD (I/R+XFZYD$_{2.7}$). Abbreviations: ONL, outer nuclear layer; OPL, outer plexiform layer; INL, inner nuclear layer; IPL, inner plexiform layer; GCL, ganglion cell layer. Scale bar=50 μm.
Figure 3F:
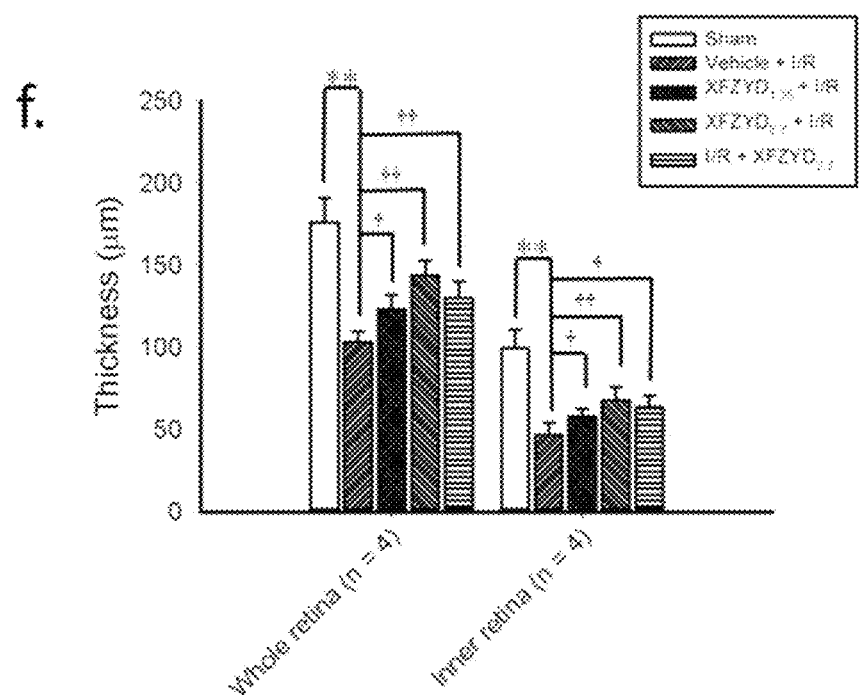
FIG. 3F shows the morphometric analysis of the thickness of the various retinal layers from sections of similar eccentricity in FIG. 3A-3E. Results indicates the mean values±SD of the number of experiments (n=4). **Significantly different (p<0.01) from the Sham retina. † or †† Significantly different (p<0.05 or p<0.01) from the Vehicle+I/R.

The result is as shown in FIG. 2A-2F. The density of RGCs in the sham retina (Sham; n=3; FIG. 2A) was 366.78±10.30 cells. As compared to the Sham retina, the density of RGCs was significantly (p<0.001) reduced to 131.83±9.78 cells/field in the rats subjected to retinal ischemia and pre-ischemia administration of vehicle (Vehicle+I/R; n=4; FIG. 2b). Moreover, this reduction was in a dose-responsive manner and significantly (p<0.001) attenuated (with a less effect at 1.35 g/kg/day) when the rats were subjected to retinal ischemia and pre-ischemia administrated with 1.35 and 2.7 g/Kg/day of XFZYD (XFZYD$_{1.35}$+I/R=191.38±9.45 cells/field, n=4, FIG. 2C; XFZYD$_{2.7}$+I/R=276.33±12.11 cells/field, n=4, FIG. 2D). Post-ischemia administration of 2.7 g/Kg/day of XFZYD also significantly (p<0.001) attenuated this ischemia-induced reduction (I/R+XFZYD$_{2.7}$=227.58±11.60 cells/field, n=4, FIG. 2E). The area of one field was approximately 0.25 mm². On the other hand, when the density of retrograde fluorogold labeled RGCs were compared, no significant (p=0.18) difference existed between the sham eye and the normal eye (n=4; 336.30±16.08).

Example 3

The Effect of XFZYD on the Thickness of the Various Retinal Layers Stained by Crystal Violet The animals were sacrificed and intracardially perfused with normal saline (w/v), the eyeballs were enucleated, fixated with 4% (w/v) paraformaldehyde and embedded in paraffin (Tissue-Tek TEC 5; Sakura, Alphen aan den Rijn, Netherlands) as well as processed for sectioning (5 μm). Retinal sections were stained with Cresyl Violet and examined under a light microscopy (Leica, Heidelberg, Germany). Retinal sections were microscopically examined and pictured at the same magnification (Ilford Pan-F plus film, 50 ASA) and the various retinal layer thickness was calculated from the photos.

To quantify the retinal ischemic injury, whole retinal thicknesses (from the inner limiting membrane to the retinal pigment epithelium layer) and inner retinal thicknesses (from the inner limiting membrane to the inner nuclear layer) were measured. All measurements were carried out 1 mm from the optic disc. Three consecutive sections per eye were averaged. A research staff was blinded to the information of the tissue to evaluate the changes in the thickness between five defined groups.

FIG. 3A-3F show results of retinal sections obtained from the same eccentricity (1 mm from disc) in four groups (n=4). As compared with the retina subjected to the sham procedure (Sham, FIG. 3A & FIG. 3F: 176.0±14.81 μm for the whole retina, 99.50±11.33 μm for the inner retina), following I/R and preadministrating the rats with vehicle, the thickness of the whole retina and the inner retina (Vehicle+I/R, FIG. 3B & FIG. 3F: 103.00±6.88 μm for the whole retina, 46.75±7.27 μm for the inner retina) were significantly (p<0.001) reduced. Moreover, this reduction was dose-dependently (with a less effect at 1.35 g/kg/day) and significantly attenuated when the rats were subjected to I/R and preadministrated with 1.35 and 2.7 g/Kg/day of XFZYD [XFZYD1.35+I/R, FIG. 3C & FIG. 3F: 123.25±8.62 μm for the whole retina (†, p=0.01), 57.75±5.06 μm for the inner retina (p=0.048); XFZYD2.7+I/R, FIG. 3D & FIG. 3F: 144.00±8.83 μm for the whole retina (p<0.001), 67.75±8.18 μm for the inner retina (p=0.009)]. Post-ischemia administration of 2.7 g/Kg/day of XFZYD also significantly attenuated this ischemia-induced decrease [I/R+XFZYD2.7, FIG. 3E & FIG. 3F: 130.25±9.98 μm for the whole retina (p=0.004), 63.50±6.95 μm for the inner retina (p=0.016)].

Example 4

The Effect of XFZYD on ChAT Immunolabeling

After sacrifice, the eyeballs were embedded in paraffin and processed for sectioning as described above. Then the sections were processed for immunohistochemical analysis using 1:100 goat anti-ChAT polyclonal antibody (Millipore, CA, USA) as primary antibodies. Afterwards, the retinal sections were incubated with 1:500 rhodamine-conjugated rabbit anti-goat antibody (Millipore, CA, USA) as secondary antibody. Simultaneously, the cellular nuclei were stained with 4,6-diamidine-2-phenylindole dihydrochloride (DAPI; EMD Chemicals, Darmstadt, Germany) as described previously (Neville N. Osborne, Robert J. Casson, John P. M. Wood, Glyn Chidlow, Mark Graham, Jose Melena. Retinal ischemia: mechanisms of damage and potential therapeutic strategies. *Progress in Retinal and Eye Research.* 2004; 23(1):91-147; Yan-Qing Chen, Wynn H. T. Pan, Jorn-Hon Liu, Mi-Mi Chen, Chi-Ming Liu, Ming-Yang Yeh, Shen-Kou Tsai, Mason Shing Young, Xiu-Mei Zhang and Hsiao-Ming Chao. The effects and underlying mechanisms of S-allyl 1-cysteine treatment of the retina after ischemia/reperfusion. *Journal of Ocular Pharmacology and Therapeutics.* 28(2): 110-117, 2012). A fluorescence microscope was utilized to evaluate the retinal samples. When it was necessary to compare the immunoreactivity in retinal tissues in various defined groups an independent scientist was required to grade the intensities by relating to the immunoreactivity in the sham group (control). Thus, prejudice was prevented as possible as it could be.

Figure 4A:
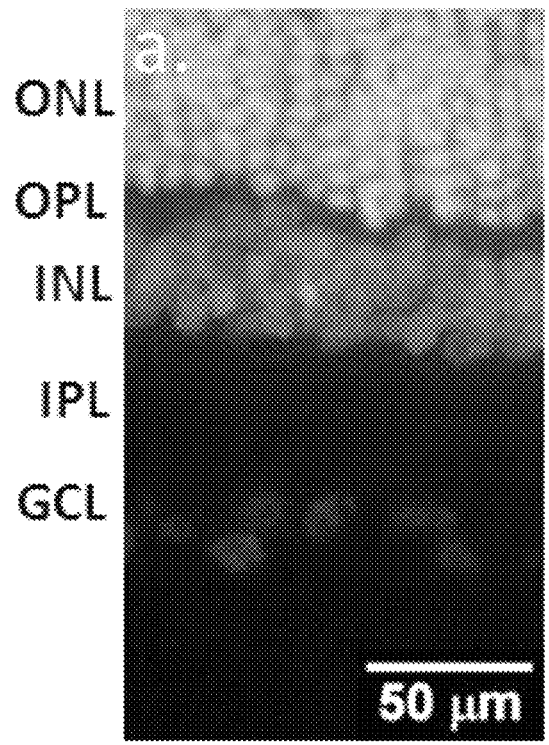
FIG. 4A is the Choline acetyltransferase (ChAT) immunohistochemistry of the retina subjected to the sham procedure (Sham) and the cellular nuclei are stained with 4,6-diamidine-2-phenylindole dihydrochloride (DAPI). Abbreviations: ONL, outer nuclear layer, OPL, outer plexiform layer, INL, inner nuclear layer, IPL, inner plexiform layer, GCL, ganglion cell layer. XFZYD, Xue-Fu-Zhu-Yu decoction. Scale bar=50 μm.
Figure 4B:
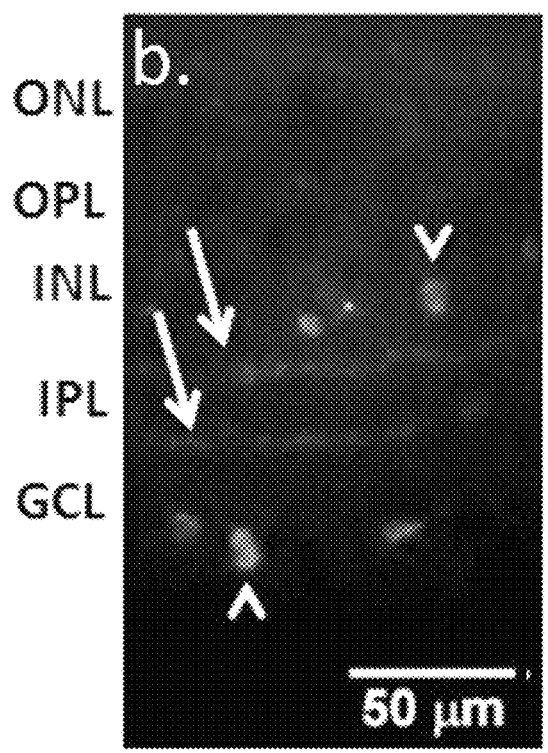
FIG. 4B is the Choline acetyltransferase (ChAT) immunohistochemistry which shows the amacrine cell bodies (Sham; arrow heads) located in the INL and the GCL and their neuronal processes (arrows) demonstrating two distinct strata in the IPL. Abbreviations: ONL, outer nuclear layer, OPL, outer plexiform layer, INL, inner nuclear layer, IPL, inner plexiform layer, GCL, ganglion cell layer. Scale bar=50 μm.
Figure 4C:
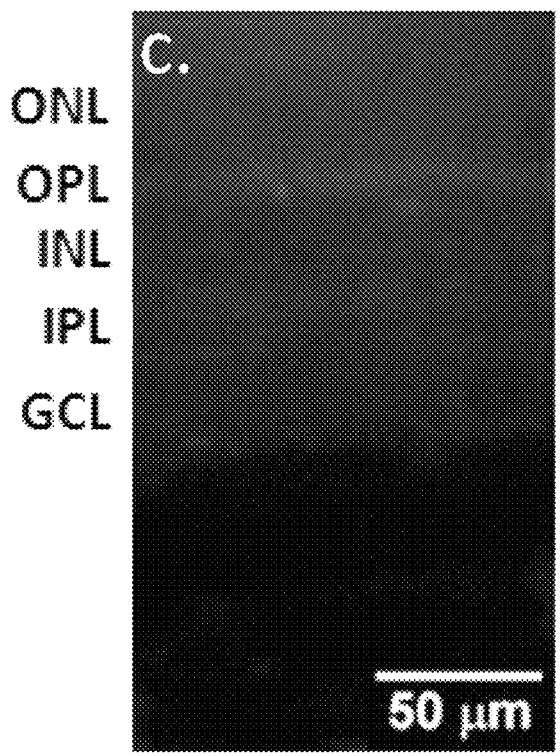
FIG. 4C is the Choline acetyltransferase (ChAT) immunohistochemistry of the retina that received I/R and preadministration of vehicle; there is a drastic decrease in the IPL immunolabeling and the amacrine cell body number. Abbreviations: ONL, outer nuclear layer, OPL, outer plexiform layer, INL, inner nuclear layer, IPL, inner plexiform layer, GCL, ganglion cell layer. Scale bar=50 μm.
Figure 4D:
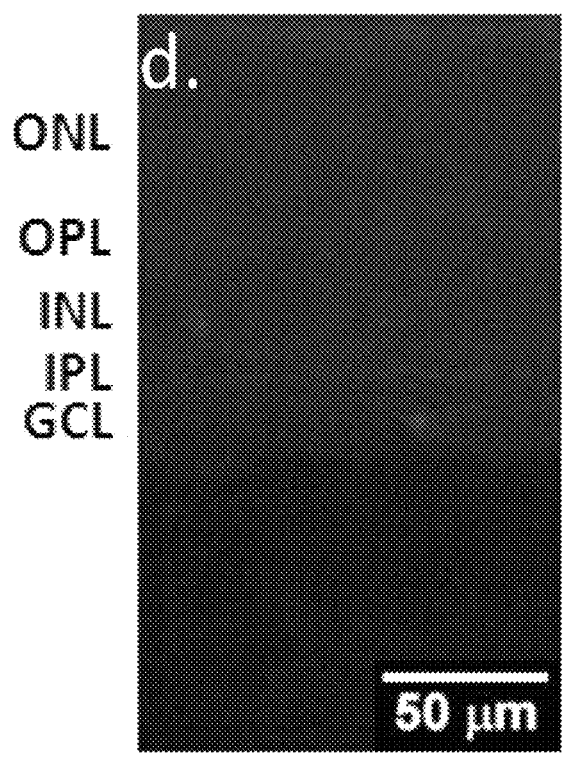
FIG. 4D is the Choline acetyltransferase (ChAT) immunohistochemistry of the section from the retinas that received I/R and preadministration of 1.35 g/kg/day of XFZYD (XFZYD$_{1.35}$+I/R) Abbreviations: ONL, outer nuclear layer, OPL, outer plexiform layer, INL, inner nuclear layer, IPL, inner plexiform layer, GCL, ganglion cell layer. Scale bar=50 μm.
Figure 4E:
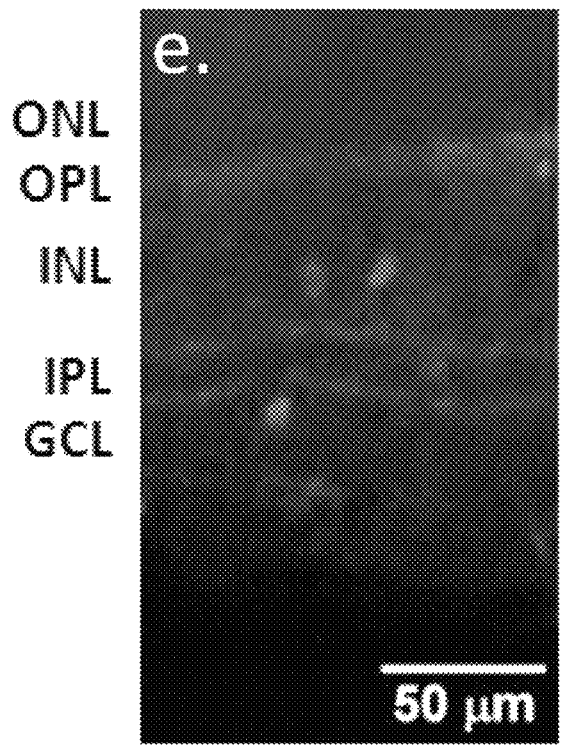
FIG. 4E is the Choline acetyltransferase (ChAT) immunohistochemistry of the section from the retinas that received I/R and preadministration of 2.7 g/kg/day of XFZYD (XFZYD$_{2.7}$+I/R). The ischemia-induced alterations were clearly and dose-dependently attenuated when ischemic retinas were preadministrated with 1.35 and 2.7 g/Kg/day of XFZYD. Abbreviations: ONL, outer nuclear layer, OPL, outer plexiform layer, INL, inner nuclear layer, IPL, inner plexiform layer, GCL, ganglion cell layer. Scale bar=50 μm.
Figure 4F:
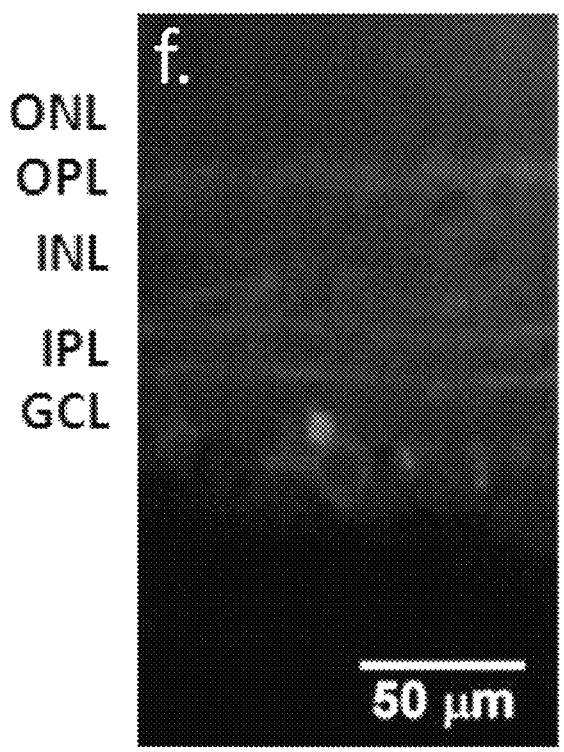
FIG. 4F is the Choline acetyltransferase (ChAT) immunohistochemistry of the section from the retinas that received I/R and postadministration of 2.7 g/kg/day of XFZYD (I/R+XFZYD$_{2.7}$). Postadministration of 2.7 g/Kg/day of XFZYD clearly attenuated these ischemia-induced alterations. Abbreviations: ONL, outer nuclear layer, OPL, outer plexiform layer, INL, inner nuclear layer, IPL, inner plexiform layer, GCL, ganglion cell layer. Scale bar=50 µm.
Figure 4G:
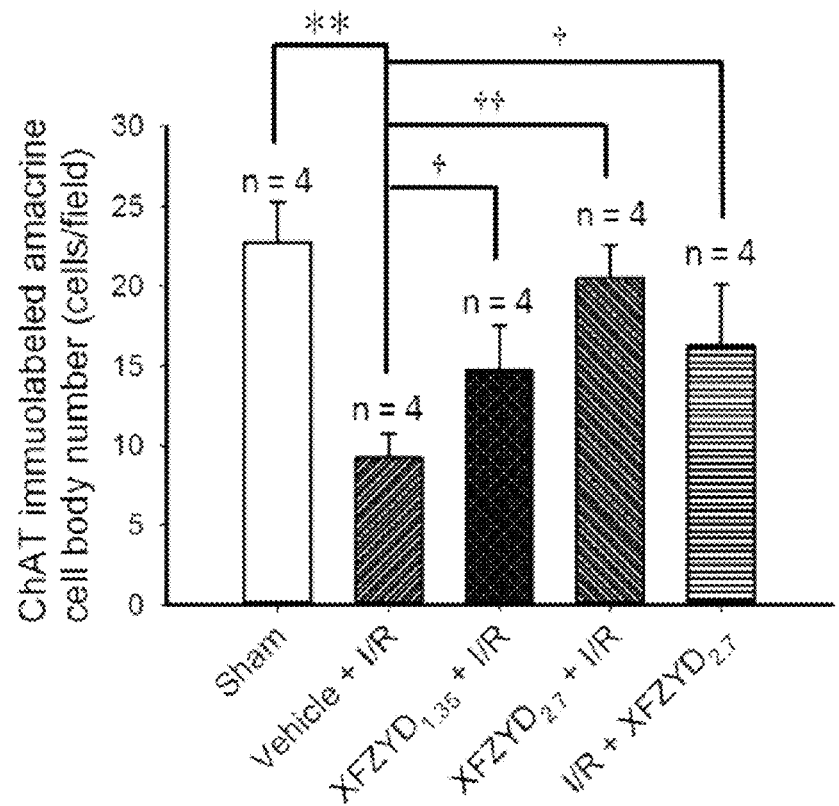
FIG. 4G is the Choline acetyltransferase (ChAT) immunolabeled amacrine cell body number (cells/field) in FIG. 4B-4F. The ischemia-induced alterations were clearly and dose-dependently attenuated when ischemic retinas were preadministrated with 1.35 and 2.7 g/Kg/day of XFZYD. Postadministration of 2.7 g/Kg/day of XFZYD clearly attenuated the ischemia-induced alterations. Each bar represents the mean value±SD (n=4) following the sham procedure or I/R. ** represents significance (p<0.01; Sham vs. Vehicle+I/R). † or †† represents significance (p<0.05 or p<0.01; Vehicle+I/R vs. XFZYD$_{1.35}$+I/R, XFZYD$_{2.7}$+I/R or I/R+XFZYD$_{2.7}$). The area of one field was approximately 0.25 mm$^2$. Abbreviations: ONL, outer nuclear layer, OPL, outer plexiform layer, INL, inner nuclear layer, IPL, inner plexiform layer, GCL, ganglion cell layer. XFZYD, Xue-Fu-Zhu-Yu decoction.
Figure 5A:
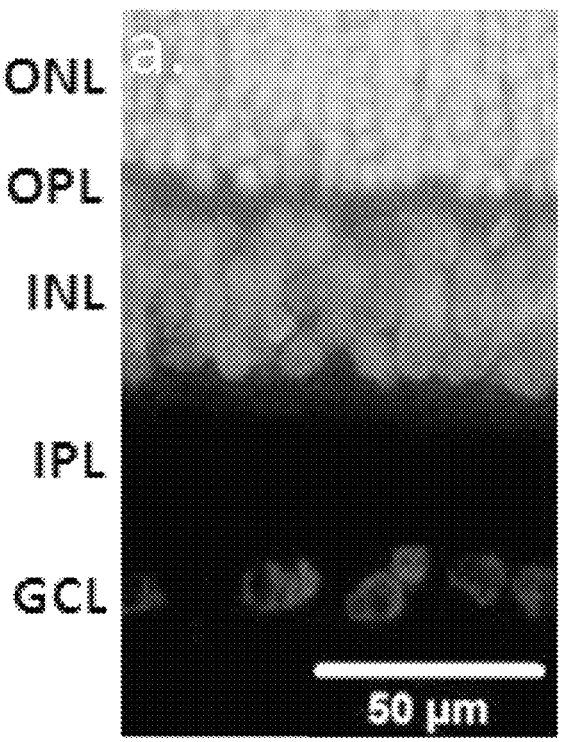
FIG. 5A is the glial fibrillary acidic protein (GFAP) immunohistochemistry. This figure shows the cellular nuclei of the sham retina stained with 4,6-diamidine-2-phenylindole dihydrochloride (DAPI). ONL: outer nuclear layer, OPL: outer plexiform layer, INL: inner nuclear layer, IPL: inner plexiform layer, GCL: ganglion cell layer. Scale bar=50 µm.
Figure 5B:
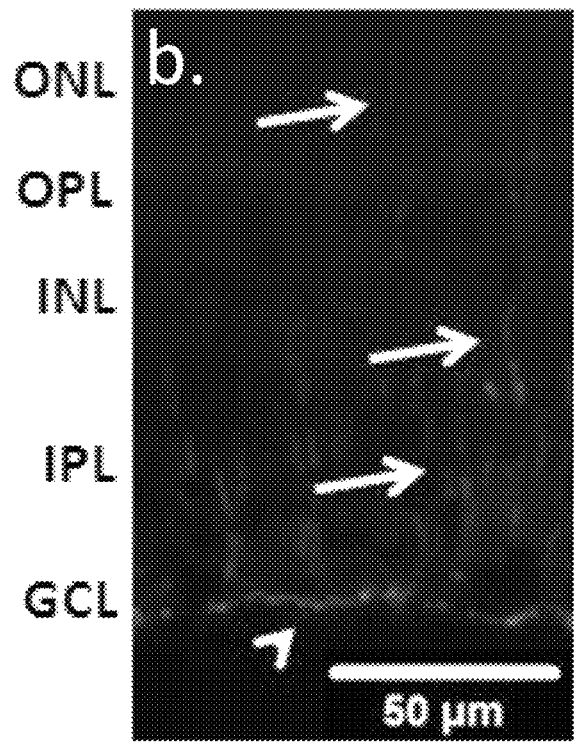
FIG. 5B is the glial fibrillary acidic protein (GFAP) immunohistochemistry. The Müller cells were demonstrated with the GFAP immunolabeling at the end feet (arrow head) in the GCL and at the processes in the IPL, INL and ONL (arrows). ONL: outer nuclear layer, OPL: outer plexiform layer, INL: inner nuclear layer, IPL: inner plexiform layer, GCL: ganglion cell layer. Scale bar=50 µm.
Figure 5C:
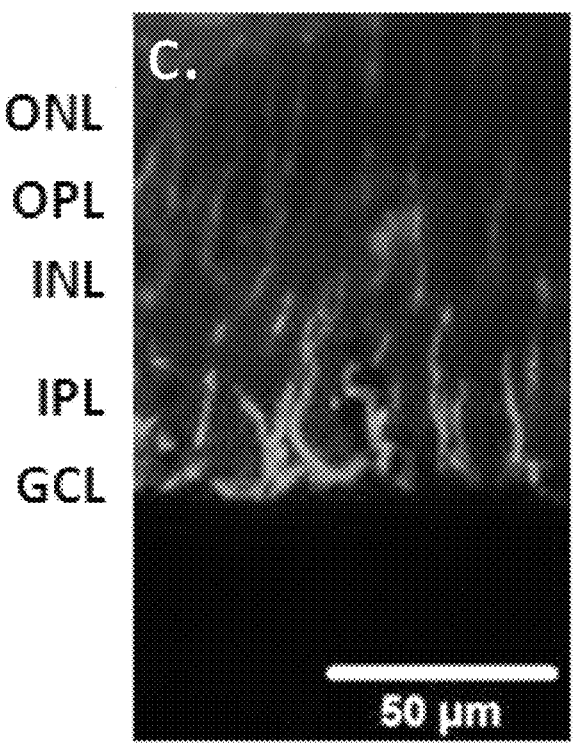
FIG. 5C is the glial fibrillary acidic protein (GFAP) immunohistochemistry. This figure demonstrates the retina that received I/R and preadminstration of vehicle; the anti-GFAP immunolabeling was increased. ONL: outer nuclear layer, OPL: outer plexiform layer, INL: inner nuclear layer, IPL: inner plexiform layer, GCL: ganglion cell layer. Scale bar=50 µm.
Figure 5D:
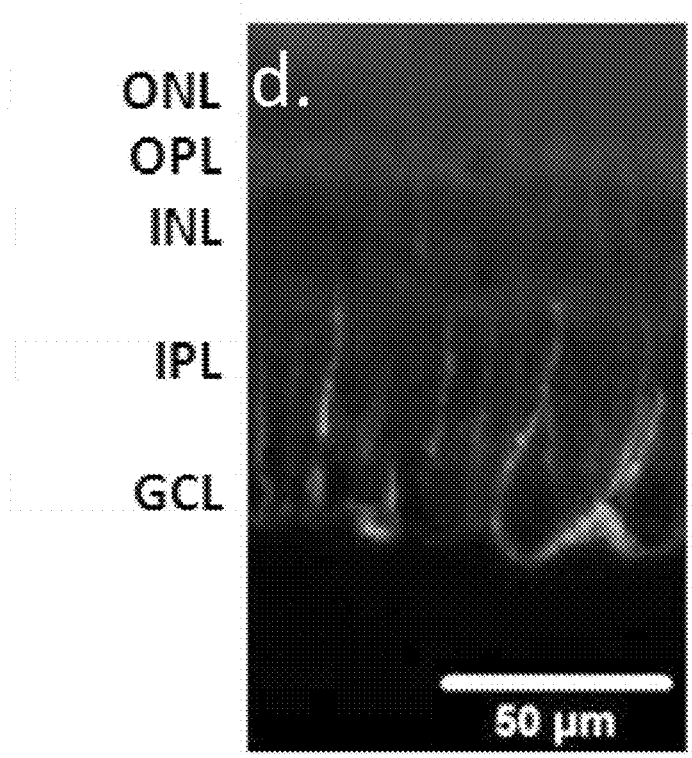
FIG. 5D is the glial fibrillary acidic protein (GFAP) immunohistochemistry. This figure shows the section from the retinas that received I/R and preadministration of 1.35 g/kg/day of XFZYD (XFZYD$_{1.35}$+I/R). ONL: outer nuclear layer, OPL: outer plexiform layer, INL: inner nuclear layer, IPL: inner plexiform layer, GCL: ganglion cell layer. Scale bar=50 µm.
Figure 5E:
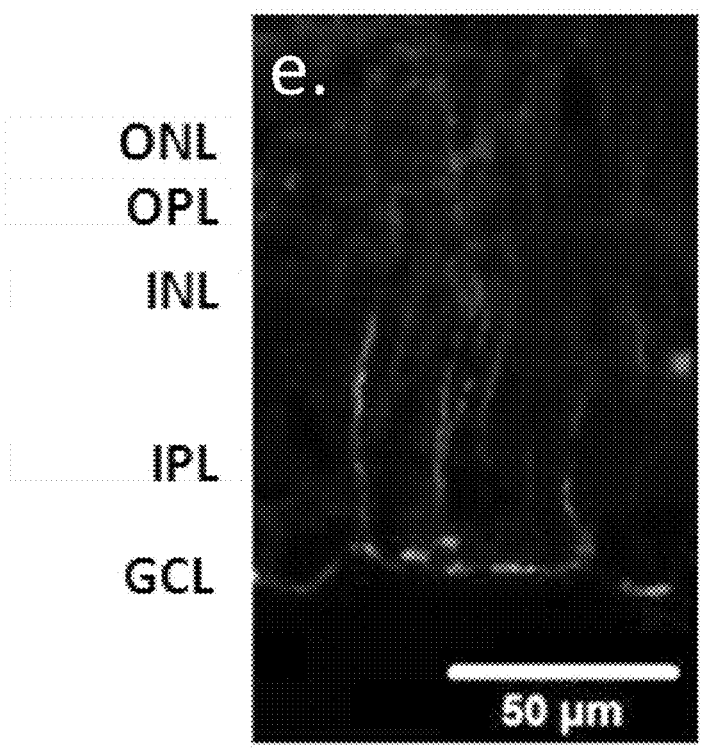
FIG. 5E is the glial fibrillary acidic protein (GFAP) immunohistochemistry. This figure shows the section from the retinas that received I/R and preadministration of 2.7 g/kg/day of XFZYD (XFZYD$_{2.7}$+I/R). The ischemia-associated alteration was obviously and dose-dependently mitigated when ischemic retinas were preadministrated with 1.35 and 2.7 g/Kg/day of XFZYD. ONL: outer nuclear layer, OPL: outer plexiform layer, INL: inner nuclear layer, IPL: inner plexiform layer, GCL: ganglion cell layer. Scale bar=50 µm.
Figure 5F:
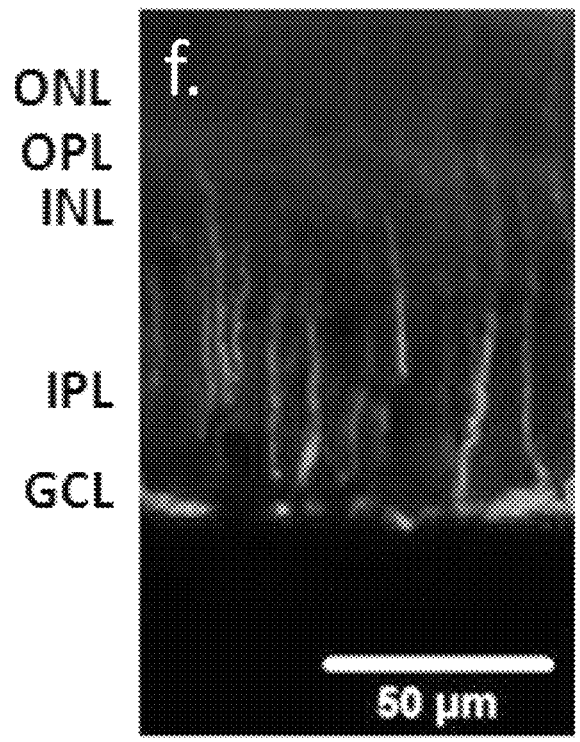
FIG. 5F is the glial fibrillary acidic protein (GFAP) immunohistochemistry. This figure shows the section from the retinas that received I/R and postadministration of 2.7 g/kg/day of XFZYD (I/R+XFZYD$_{2.7}$). Postadministration of 2.7 g/Kg/day of XFZYD obviously mitigated the ischemia-induced alteration. ONL: outer nuclear layer, OPL: outer plexiform layer, INL: inner nuclear layer, IPL: inner plexiform layer, GCL: ganglion cell layer. Scale bar=50 µm.

As shown in FIG. 4A-4G, in the retina subjected to the sham procedure (Sham, FIG. 4B), ChAT immunoreactivity labeled the amacrine cell bodies (arrow heads; FIG. 4G: 22.75±2.50) in the inner nuclear layer (INL) and the ganglion cell layer (GCL); and their neuronal processes displayed two well-delineated bands (arrows) in the inner plexiform layer (IPL). In the ischemic retina preadministrated with vehicle (Vehicle+I/R; FIG. 4C), the CHAT-labeled amacrine cell bodies (FIG. 4G: 9.25±1.50) were significantly (p<0.001) less numerous following retinal I/R and pre-ischemia administration of vehicle; moreover, the IPL immunoreactivity of these cells was drastically decreased. Clinically importantly, these alterations were dose-dependently and significantly attenuated when the ischemic retinas were preadministrated with 1.35 and 2.7 g/Kg/day of XFZYD (XFZYD1.35+I/R, FIGS. 4D and 4G: 14.75±2.75, p=0.013); XFZYD2.7+I/R, FIGS. 4E and 4G: 20.50±2.08, p<0.001). Post-ischemia administration of 2.7 g/Kg/day of XFZYD (I/R+XFZYD2.7, FIGS. 4F and 4G: 16.25±3.86, P=0.015) also clearly attenuated these ischemia-induced alterations. DAPI (FIG. 4A) was utilized to stain the cellular nuclei in the Sham retina. The area of one field was approximately 0.25 mm$^2$.

Example 5

The Effect of XFZYD on GFAP or Vimentin Immunolabeling

After sacrifice, the eyeballs were embedded in paraffin and processed for sectioning as described above. Then the sections were processed for immunohistochemical analysis using the following primary antibodies: 1:100 rabbit anti-GFAP polyclonal antibody (Millipore, CA, USA) or 1:100 mouse anti-vimentin monoclonal antibody (Sigma-Aldrich, MO, USA). Afterwards, the retinal sections were incubated with secondary antibody: 1:500 fluorescein isothiocyanate (FITC)-conjugated goat anti-rabbit IgG (Millipore, CA, USA) or 1:500 FITC-conjugated goat antimouse IgG (Millipore, CA, USA). Simultaneously, the cellular nuclei were stained with 4,6-diamidine-2-phenylindole dihydrochloride (DAPI; EMD Chemicals, Darmstadt, Germany) as described previously (Neville N. Osborne, Robert J. Casson, John P. M. Wood, Glyn Chidlow, Mark Graham, Jose Melena. Retinal ischemia: mechanisms of damage and potential therapeutic strategies. *Progress in Retinal and Eye Research.* 2004; 23(1):91-147; Yan-Qing Chen, Wynn H. T. Pan, Jorn-Hon Liu, Mi-Mi Chen, Chi-Ming Liu, Ming-Yang Yeh, Shen-Kou Tsai, Mason Shing Young, Xiu-Mei Zhang and Hsiao-Ming Chao. The effects and underlying mechanisms of S-allyl 1-cysteine treatment of the retina after ischemia/ reperfusion. *Journal of Ocular Pharmacology and Therapeutics.* 28(2): 110-117, 2012). A fluorescence microscope was utilized to evaluate the retinal samples as described previously. When it was necessary to compare the immunoreactivity in retinal tissues in various defined groups an independent scientist was required to grade the intensities by relating to the immunoreactivity in the sham group (control). Thus, prejudice was prevented as possible as it could be.

As shown in FIG. 5A-5F, in the Sham retina (FIG. 5B), the Müller cells were revealed with the GFAP immunolabelings at the end feet (arrow head) in the GCL and at the processes that extended into the IPL, INL and ONL (arrows). In the ischemic retina preadministrated with vehicle (Vehicle+I/R, FIG. 5C), the anti-GFAP immunolabeling was enhanced. Moreover, this alteration was clearly and dose-dependently attenuated when the ischemic retinas were preadministrated with 1.35 and 2.7 g/Kg/day of XFZYD (XFZYD$_{1.35}$+I/R, FIG. 5D; XFZYD$_{2.7}$+I/R, FIG. 5E). Post-ischemia administration of 2.7 g/Kg/day of XFZYD (I/R+XFZYD$_{2.7}$, FIG. 5F) also clearly attenuated this ischemia-induced alteration. DAPI (FIG. 5a) was utilized to stain the cellular nuclei of the Sham retina.

Figure 6A:
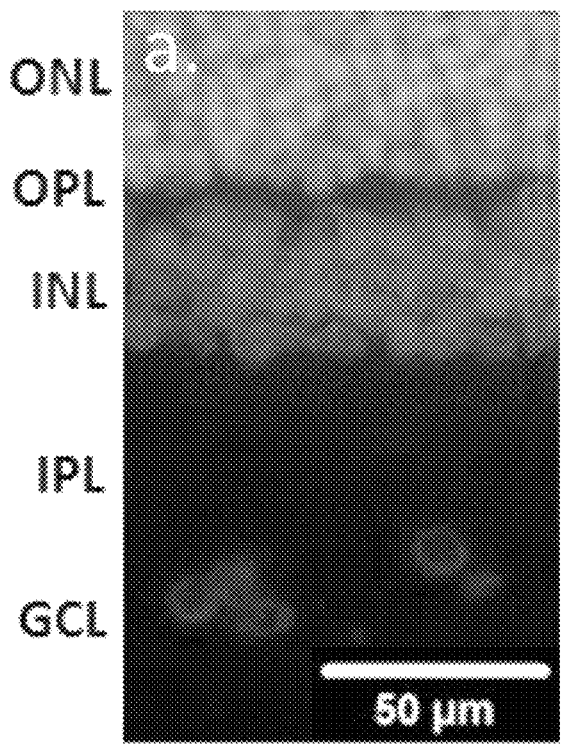
FIG. 6A is the vimentin immunohistochemistry. This figure shows the cellular nuclei of the sham retina stained with 4,6-diamidine-2-phenylindole dihydrochloride (DAPI). ONL: outer nuclear layer, OPL: outer plexiform layer, INL: inner nuclear layer, IPL: inner plexiform layer, GCL: ganglion cell layer. Scale bar=50 µm.
Figure 6B:
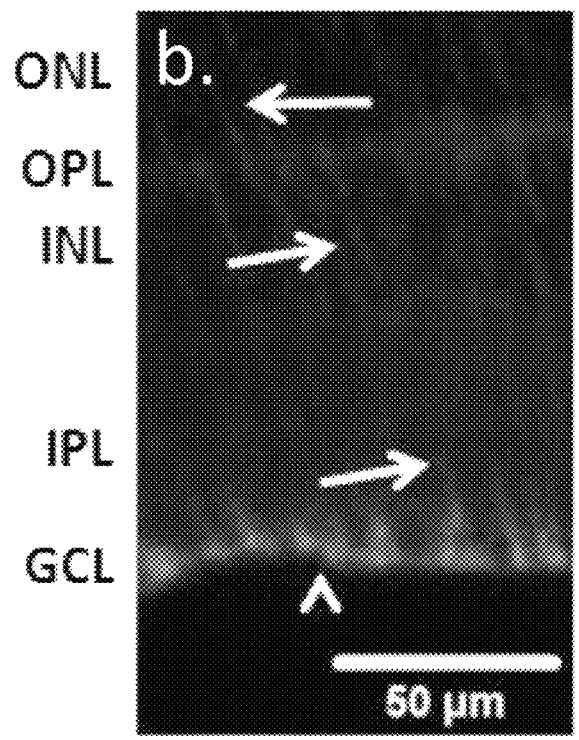
FIG. 6B is the vimentin immunohistochemistry. This figure demonstrates the sham retina with the vimentin immunolabeling at the end feet (arrow heads) in the ganglion cell layer and at the processes in the IPL, INL and ONL (arrows). ONL: outer nuclear layer, OPL: outer plexiform layer, INL: inner nuclear layer, IPL: inner plexiform layer, GCL: ganglion cell layer. Scale bar=50 µm.
Figure 6C:
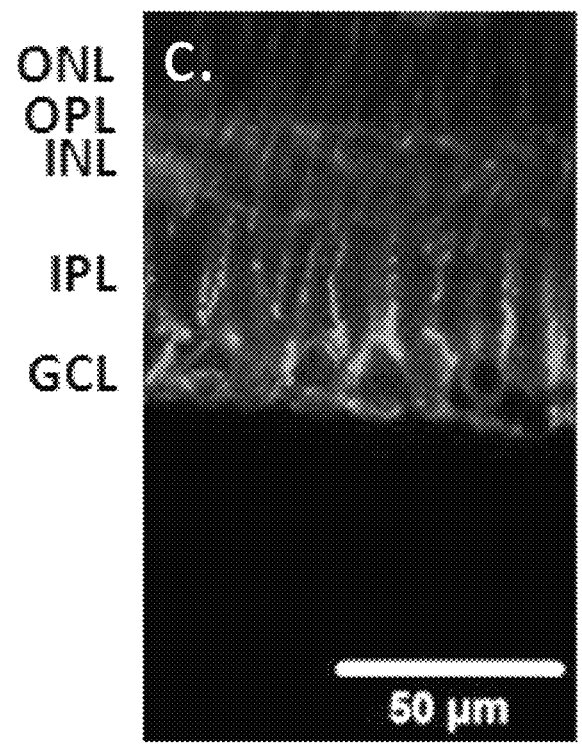
FIG. 6C is the vimentin immunohistochemistry. This figure reveals the retina that received I/R and preadminstration of vehicle; in contrast with the sham retina, the anti-vimentin immunolabeling was increased. ONL: outer nuclear layer, OPL: outer plexiform layer, INL: inner nuclear layer, IPL: inner plexiform layer, GCL: ganglion cell layer. Scale bar=50 µm.
Figure 6D:
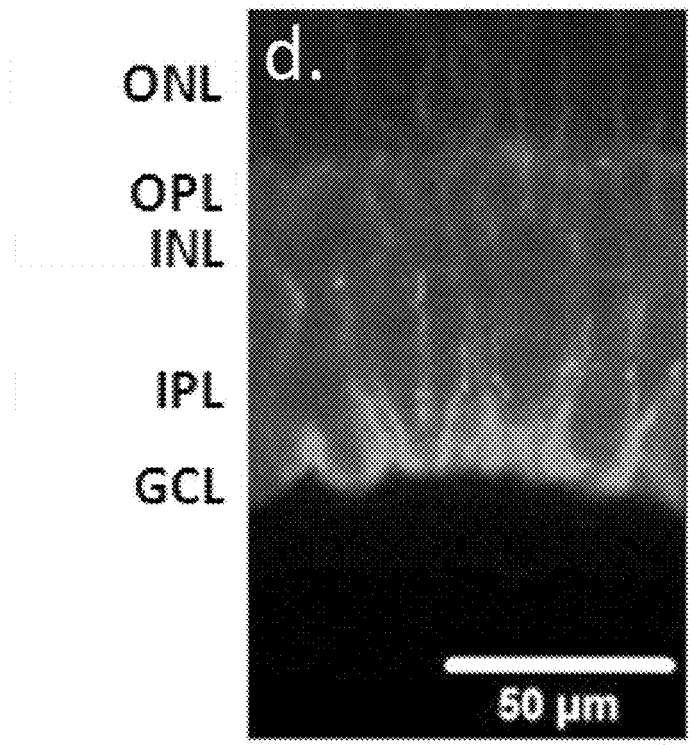
FIG. 6D is the vimentin immunohistochemistry. This figure is the section from the retina that received I/R and preadministration of 1.35 g/kg/day of XFZYD (XFZYD$_{1.35}$+I/R). ONL: outer nuclear layer, OPL: outer plexiform layer, INL: inner nuclear layer, IPL: inner plexiform layer, GCL: ganglion cell layer. Scale bar=50 µm.
Figure 6E:
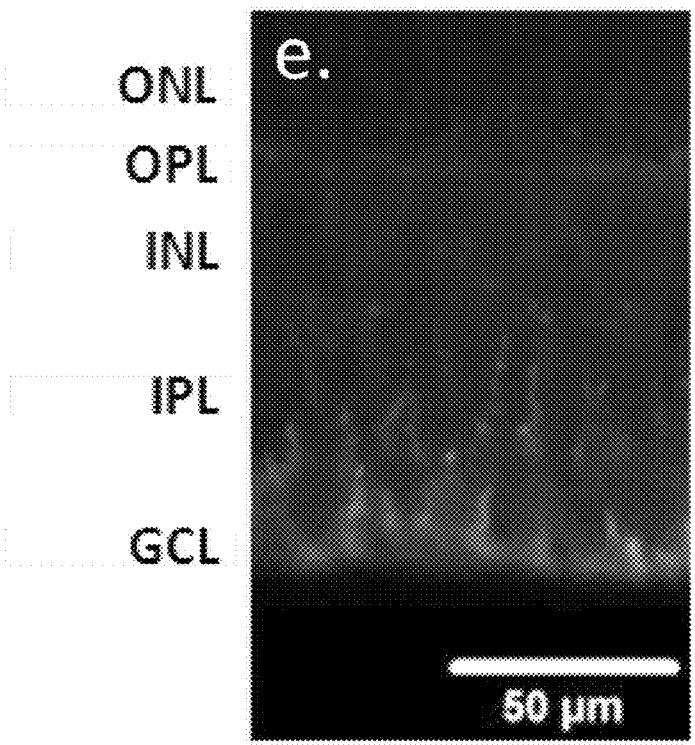
FIG. 6E is the vimentin immunohistochemistry. This figure is the section from the retina that received I/R and preadministration of 2.7 g/kg/day of XFZYD (XFZYD$_{2.7}$+I/R). The ischemia-induced alteration was clearly and dose-dependently blunted when ischemic retinas were preadministrated with 1.35 and 2.7 g/Kg/day of XFZYD. ONL: outer nuclear layer, OPL: outer plexiform layer, INL: inner nuclear layer, IPL: inner plexiform layer, GCL: ganglion cell layer. Scale bar=50 µm.
Figure 6F:
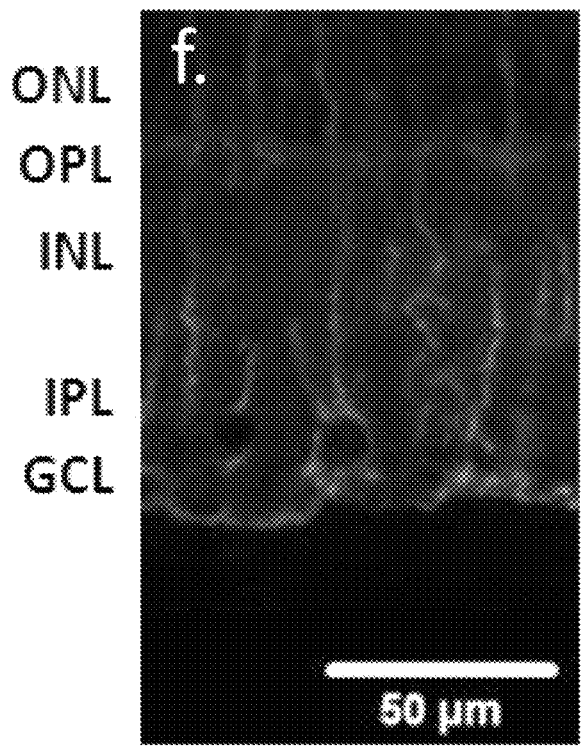
FIG. 6F is the vimentin immunohistochemistry. This figure is the section from the retina that received I/R and postadministration of 2.7 g/kg/day of XFZYD (f, I/R+XFZYD$_{2.7}$). Postadministration of 2.7 g/Kg/day of XFZYD clearly attenuated the ischemia-induced alteration. ONL: outer nuclear layer, OPL: outer plexiform layer, INL: inner nuclear layer, IPL: inner plexiform layer, GCL: ganglion cell layer. Scale bar=50 µm.
Figure 7A:
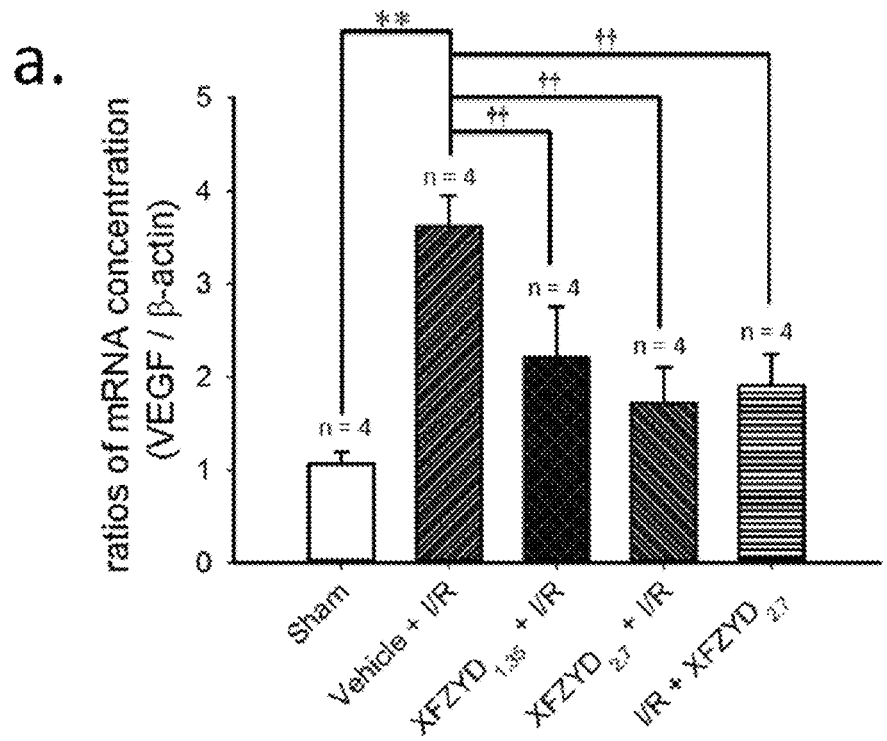
FIG. 7A shows the ratios of the mRNA concentrations of VEGF relative to that of β-actin. Total mRNA was extracted/isolated from the sham retinas or the ischemic retinas pretreated with vehicle, low (1.35 g/Kg/day)/high dose (2.7 g/kg/day) of XFZYD, or posttreated with high dose of XFZUD. The ratios of the mRNA concentrations of VEGF relative to that of β-actin were calculated. Each bar indicates the mean±SD (n=4). ** (p<0.01) represents significance (Sham vs. Vehicle+I/R). †† (<0.01) represents significance (Vehicle+I/R vs. XFZYD$_{1.35}$+I/R, XFZYD$_{2.7}$+I/R, or I/R+XFZYD$_{2.7}$). VEGF: vascular endothelial growth factor.
Figure 7B:
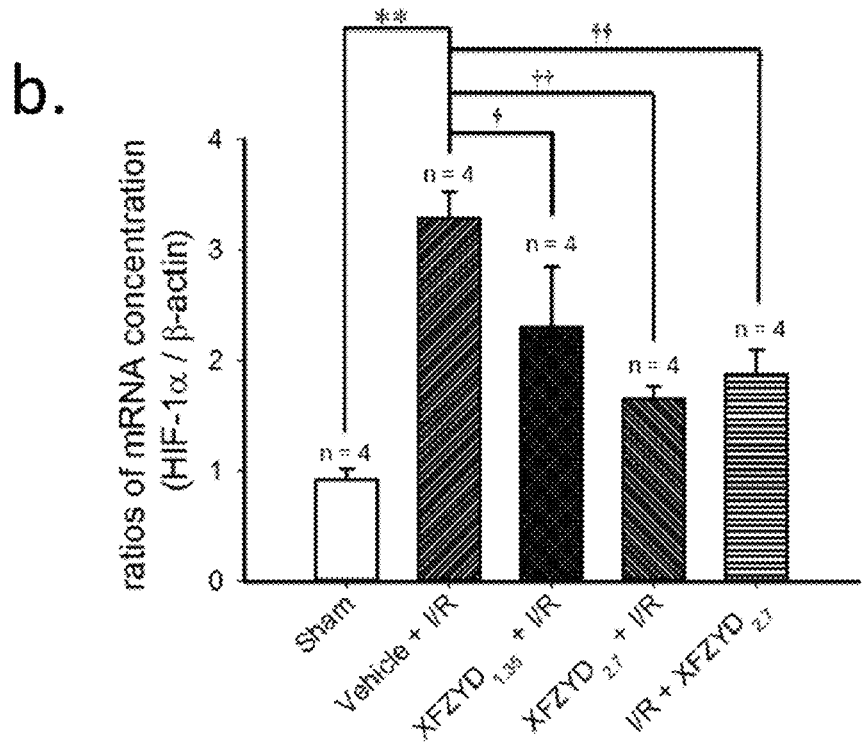
FIG. 7B shows the ratios of the mRNA concentrations of HIF-1α relative to that of β-actin. Total mRNA was extracted/isolated from the sham retinas or the ischemic retinas pretreated with vehicle, low (1.35 g/Kg/day)/high dose (2.7 g/kg/day) of XFZYD, or posttreated with high dose of XFZUD. The ratios of the mRNA concentrations of HIF-1α relative to that of β-actin were calculated. Each bar indicates the mean±SD (n=4). ** (p<0.01) represents significance (Sham vs. Vehicle+I/R). † (p<0.05) or †† (<0.01) represents significance (Vehicle+I/R vs. XFZYD$_{1.35}$+I/R, XFZYD$_{2.7}$+I/R, or I/R+XFZYD$_{2.7}$). HIF-1α: hypoxia inducible factor 1α.
Figure 7C:
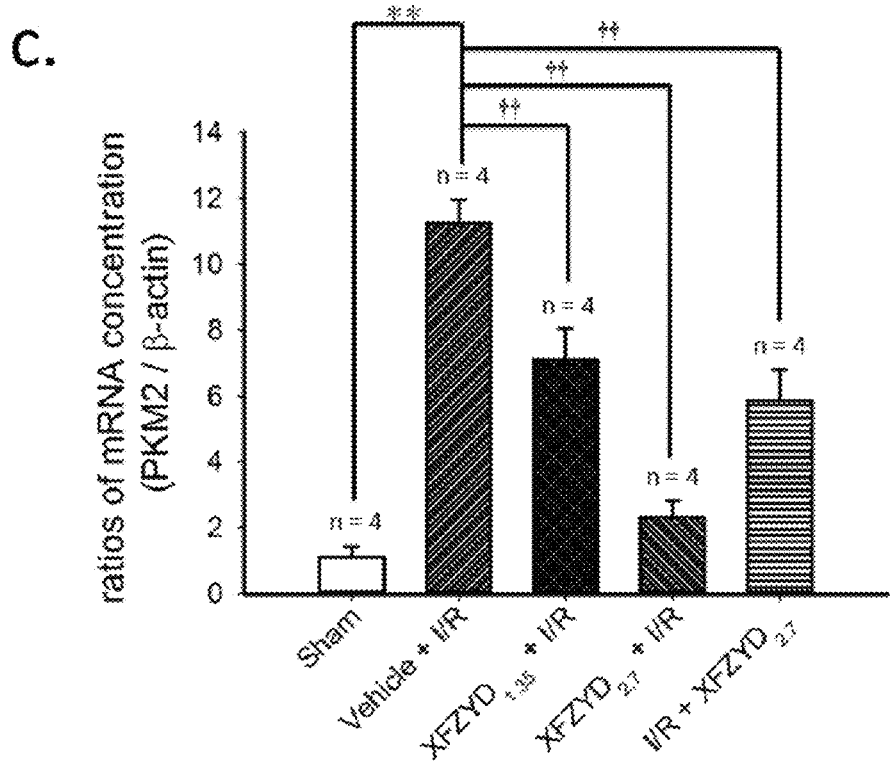
FIG. 7C shows the ratios of the mRNA concentrations of PKM2 to that of β-actin. Total mRNA was extracted/isolated from the sham retinas or the ischemic retinas pretreated with vehicle, low (1.35 g/Kg/day)/high dose (2.7 g/kg/day) of XFZYD, or posttreated with high dose of XFZYD. The ratios of the mRNA concentrations of PKM2 relative to that of β-actin were calculated. Each bar indicates the mean±SD (n=4). ** (p<0.01) represents significance (Sham vs. Vehicle+I/R). †† (<0.01) represents significance (Vehicle+I/R vs. XFZYD$_{1.35}$+I/R, XFZYD$_{2.7}$+I/R, or I/R+XFZYD$_{2.7}$). PKM2: pyruvate kinase M2.
Figure 7D:
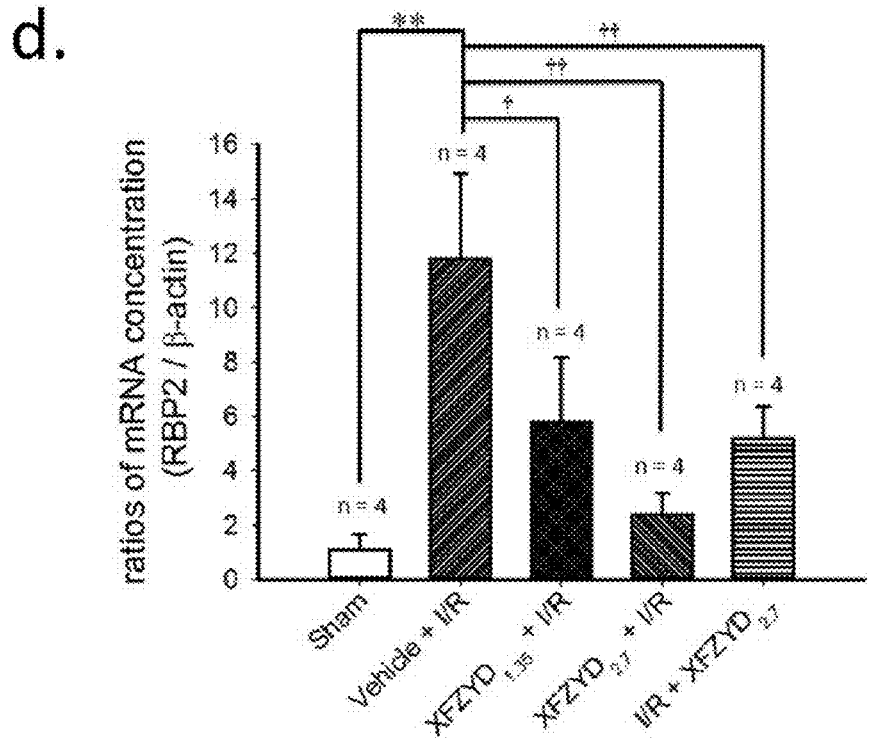
FIG. 7D shows the ratios of the mRNA concentrations of RBP2 relative to that of β-actin. Total mRNA was extracted/isolated from the sham retinas or the ischemic retinas pretreated with vehicle, low (1.35 g/Kg/day)/high dose (2.7 g/kg/day) of XFZYD, or posttreated with high dose of XFZYD. The ratios of the mRNA concentrations of RBP2 relative to that of β-actin were calculated, respectively. Each bar indicates the mean±SD (n=4). ** (p<0.01) represents significance (Sham vs. Vehicle+I/R). † (p<0.05) or †† (<0.01) represents significance (Vehicle+I/R vs. XFZYD$_{1.35}$+I/R, XFZYD$_{2.7}$+I/R, or I/R+XFZYD$_{2.7}$). RBP2: retinoblastoma-binding protein 2.

DAPI (FIG. 6A) was utilized to stain the cellular nuclei of the Sham retina. When compared with the control retina (Sham, FIG. 6B), anti-vimentin immunoreactivity was also enhanced after retinal ischemia and pre-ischemia administration of vehicle (Vehicle+I/R, FIG. 6C). This enhancement was drastically and in a dose-responsive manner counteracted by pre-ischemia administration of 1.35 and 2.7 g/Kg/day of XFZYD (XFZYD$_{1.35}$+I/R, FIG. 6D; XFZYD$_{2.7}$+I/R, FIG. 6E). Post-ischemia administration of 2.7 g/Kg/day of XFZYD (I/R+XFZYD$_{2.7}$, FIG. 6F) also considerably obliterated this ischemia-induced alteration.

Example 6

The Effect of XFZYD on the Retinal mRNA Levels of VEGF, HIF-1α, PKM2 and RBP2

The levels of VEGF, HIF-1α, PKM2 and RBP2 mRNAs present in the retinas were determined using a real-time PCR technique. Twenty-four hours after retinal ischemia and pre-/post-ischemia administration of the defined chemicals or after a sham procedure, the rats were sacrificed and the retinas were removed. This was followed by sonication in Tri Reagent (Sigma, Missouri, USA). Retinal RNA was isolated and first strand complementary DNA (cDNA) synthesis was performed on 2 μg RQ1 RNase-Free DNase (0.05 U/μl; Promega)-treated RNA using High Capacity RNA-to-cDNA Master Mix (Applied Biosystems, MA, USA). The first-strand cDNA then underwent real-time PCR using Fast Smart Quant Green Master Mix (Bio-protech, Gangwon-do, Korea). The PCR was initiated by incubation at 95° C. for 20 second; then 40 cycles of 95° C. for 3 second and 60° C. for 30 second were performed. Cycling was carried out on a StepOne Plus™ Real-Time PCR System (Applied Biosystems, MA, USA). Relative quantification (a comparative method) was performed using the house keeping gene β-actin as the internal standard. This process allows the normalized quantification of the target mRNA and takes into account the differences in the amount of total RNA added to each reaction (ΔCt=Ct target-Ct β-actin; cycle threshold, Ct). The relative VEGF/HIF-1α/PKM2/RBP2 level changes induced by ischemia or sham procedure were calculated as fold variations relative to the contralateral untreated control normal retina with respect to the calibrator (Ct=ΔCt induced-ΔCt normal). Relative quantification of gene expression was calculated according to the 2-ΔΔCt method as described in the manufacturer's instructions (Hsiao-Ming Chao, Min-Jay Chuang, Jorn-Hon Liu, Xiao-Qian Liu, Li-Kang Ho, Wynn H. T. Pan, Xiu-Mei Zhang, Chi-Ming Liu, Shen-Kou Tsai, Chi-Woon Kong, Shou-Dong Lee, Mi-Mi Chen, and Fang-Ping Chao. Baicalein protects against retinal ischemia by antioxidation, antiapoptosis, downregulation of HIF-1α, VEGF, and MMP-9 and upregulation of HO-1. *Journal of Ocular Pharmacology and Therapeutics.* 29(6): 539-549, 2013; Hsiao-Ming Chao, Ing-Ling Chen and Jorn-Hon Liu. S-allyl L-cysteine protects the retina against kainate excitotoxicity in the rat. *The American Journal of Chinese Medicine.* 2014; 42(3):693-708). The data obtained for each treatment were pooled, and a total percentage change relative to the control (Sham) was calculated. The PCR oligonucleotide primers were obtained from Mission Biotech (Taipei, Taiwan) as follows:

Beta-actin forward primer:

5'-AGGGAAATCGTGCGTGACAT-3';            (SEQ ID No: 1)

Beta-actin reverse primer:

5'-GAACCGCTCATTGCCGATAG-3';            (SEQ ID No: 2)

VEGF forward primer for PCR:

5'-GCGGGCTGCTGCAATG-3';                (SEQ ID No: 3)

VEGF reverse primer for PCR:

5'-TGCAACGCGAGTCTGTGTTT-3';            (SEQ ID No: 4)

HIF-1alpha forward primer for PCR:

5'-ACAGCTCCCCAGCATTTCAC-3';            (SEQ ID No: 5)

HIF-1alpha reverse primer for PCR:

5'-GGACAAACTCCCTCACCAAAAA-3';          (SEQ ID No: 6)

PKM2 forward primer for PCR:

5'-TCTACGTGGACGATGGGCT-3';             (SEQ ID No: 7)

PKM2 reverse primer for PCR:

5'-AGGAAGACCTTCTCTGCCGGA-3';           (SEQ ID No: 8)

RBP2 forward primer for PCR:

5'-TTGTGGTGACGTTTCCTCGT-3';            (SEQ ID No: 9)

RBP2 reverse primer for PCR:

5'-CAGCCAGCCCCACATCTAAG-3'             (SEQ ID No: 10)

As shown in FIG. 7A-7D (n=4), in contrast with the control retina (Sham; VEGF=1.06±0.13, HIF-1α=0.92±0.10, PKM2=1.10±0.33, RBP2=1.09±0.56), the ratios for VEGF (FIG. 7A), HIF-1α (FIG. 7B), PKM2 (FIG. 7C) and RBP2 (FIG. 7D) in the ischemic retina preadministrated with vehicle (Vehicle+I/R; VEGF=3.62±0.33, HIF-1α=3.29±0.24, PKM2=11.25±0.71, RBP2=11.80±3.14) were significantly (p<0.001) elevated. Moreover, this increase was in a dose dependent manner (with a less effect at 1.35 g/kg/day) and significantly [XFZYD$_{1.35}$+I/R (VEGF=2.2±0.55, p=0.005; HIF-1α=2.30±0.55, p=0.016; PKM2=7.11±0.93, p<0.001; RBP2=5.80±2.37, p=0.023); XFZYD$_{2.7}$ (VEGF=1.7±0.38, HIF-1α=1.65±0.12, PKM2=2.32±0.51, p<0.001; RBP2=2.39±0.77, p=0.001)] counteracted when the ischemic retinas were preadministrated with 1.35 and 2.7 g/Kg/day of XFZYD. Post-ischemia administration of 2.7 g/Kg/day of XFZYD also significantly [I/R+XFZYD$_{2.7}$ (VEGF=1.90±0.34, HIF-1α=1.87±0.22, PKM2=5.86±0.95, p<0.001; RBP2=5.19±1.17, p=0.008)] mitigated this ischemia-induced increase. On the other hand, when the retinal mRNA levels of VEGF, HIF-1α, PKM2 and RBP2 were compared, no significant difference existed between the sham eye and the normal eye (n=4; VEGF=1.02±0.11, p=0.36; HIF-1α=1.00±0.03, p=0.20; PKM2=1.02±0.13, p=0.36; RBP2=1.00±0.04, p=0.39).

Example 7

The Effect of XFZYD on the Concentrations of In Vivo Retinal Proteins

Twenty-four hours after retinal ischemia and pre-/post-ischemia administration of the defined chemicals or after a sham procedure, the rats were sacrificed. The retinas were removed and sonicated in lysis buffer, namely mammalian protein extraction reagent (HyCell, Taipei, Taiwan). Equal amounts of denatured protein (100 μg/32 μl/well) were separated by NuPAGE® Tris-Acetate mini gel electrophoresis (Invitrogen, MA, USA) using 3~8% separating and 3.2% stacking gels as described previously (Jorn-Hon Liu, Hsiung Wann, Mi-Mi Chen, Wynn H. T. Pan, Yei-Ching Chen, Chi-Ming Liu, Ming-Yang Yeh, Shen-Kou Tsai, Mason Shing Young, Hui-Yen Chuang, Fang-Ping Chao, and Hsiao-Ming Chao. Baicalein significantly protects human retinal pigment epithelium cells against $H_2O_2$-induced oxidative stress by scavenging reactive oxygen species and downregulating the expression of matrix metalloproteinase-9 and vascular endothelial growth factor. *Journal of Ocular Pharmacology and Therapeutics.* 2010; 26(5): 421-429; Hsiao-Ming Chao, Min-Jay Chuang, Jorn-Hon Liu, Xiao-Qian Liu, Li-Kang Ho, Wynn H. T. Pan, Xiu-Mei Zhang, Chi-Ming Liu, Shen-Kou Tsai, Chi-Woon Kong, Shou-Dong Lee, Mi-Mi Chen, and Fang-Ping Chao. Baicalein protects against retinal ischemia by antioxidation, antiapoptosis, downregulation of HIF-1α, VEGF, and MMP-9 and upregulation of HO-1. *Journal of Ocular Pharmacology and Therapeutics.* 29(6): 539-549, 2013). The separated proteins were transferred to a polyvinylidene difluoride (PVDF) membrane (Millipore, MA, USA). The membranes were then blocked for 1 hour at room temperature with 5% fat-free skimmed milk (Fonterra, Taoyuan, Taiwan) in phosphate-buffered saline (PBS). Next, the blots were incubated individually overnight at 4° C. with one of the following primary antibodies, namely, mouse monoclonal anti-β-actin antibody (1:80000, Novusbio, MA, USA), mouse monoclonal anti-VEGF antibody (1:200, Novusbio, MA, USA), mouse monoclonal anti-HIF-1α antibody (1:1000, Abcom, Cambridge, UK), rabbit polyclonal anti-PKM2 antibody (1:600, Abcom, Cambridge, UK) and rabbit monoclonal anti-RBP2 antibody (1:500, Abcom, Cambridge, UK). The blots were then incubated in the secondary antibody, either horseradish peroxidase (HRP)-conjugated goat anti-rabbit or antimouse IgG (1:2000 or 1:10000, Santa Cruz Biotechnology, TX, USA) as appropriate at 37° C. for 1 h. The primary/secondary antibodies were diluted in 5% fat-free skimmed milk. Finally, the membranes were developed using the enhanced chemiluminescent analysis system (HyCell, Taipei, Taiwan), and exposed to an X-ray film (Fujifilm, Tokyo, Japan). Scanning densitometry was used to analyze the amount of each protein present.

Figure 8A:
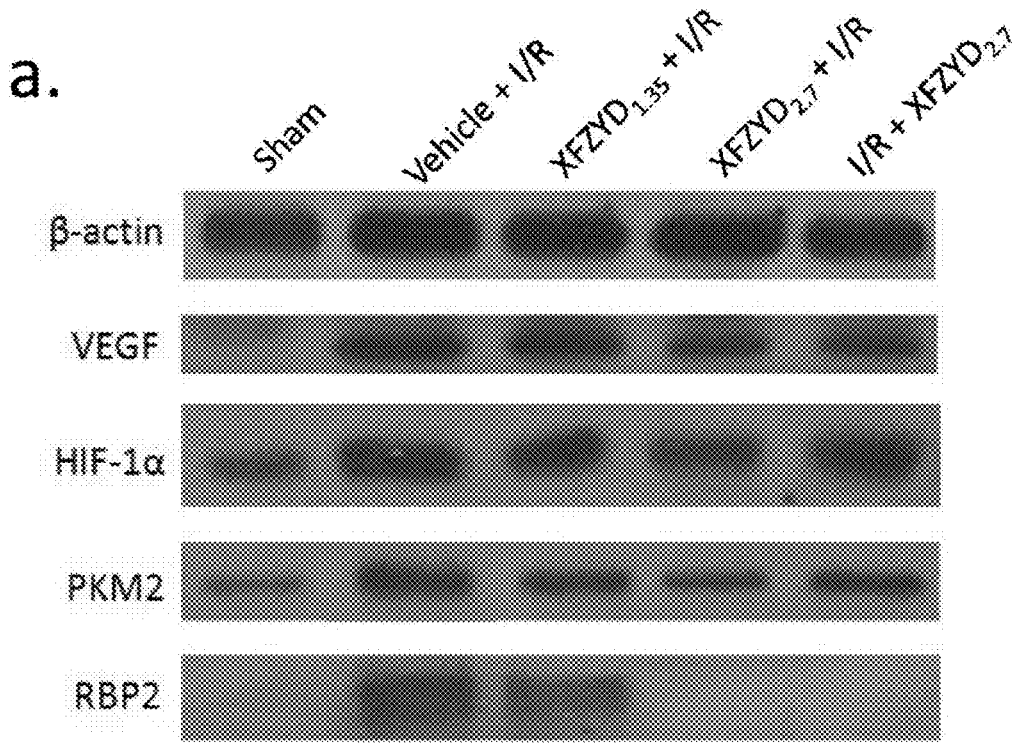
FIG. 8A shows the ratios of the protein expression levels of VEGF, HIF-1α, PKM2 or RBP2 relative to that of β-actin. This figure shows the western blotting for expressions of β-actin, VEGF, HIF-1α, PKM2 and RBP2. Lane 1 is the retina that received the sham procedure (Sham); Lane 2 is the vehicle-pretreated ischemic retina (Vehicle+I/R); Lane 3~5 are from retinas that received ischemia plus reperfusion and were preadministrated with 1.35 g/kg/day (XFZYD$_{1.35}$+I/R), 2.7 g/kg/day (XFZYD$_{2.7}$+I/R) or postadministrated with 2.7 g/kg/day (I/R+XFZYD$_{2.7}$) of XFZYD, respectively. VEGF: vascular endothelial growth factor, HIF-1α: hypoxia inducible factor 1α, PKM2: pyruvate kinase M2, RBP2: retinoblastoma-binding protein 2.
Figure 8B:
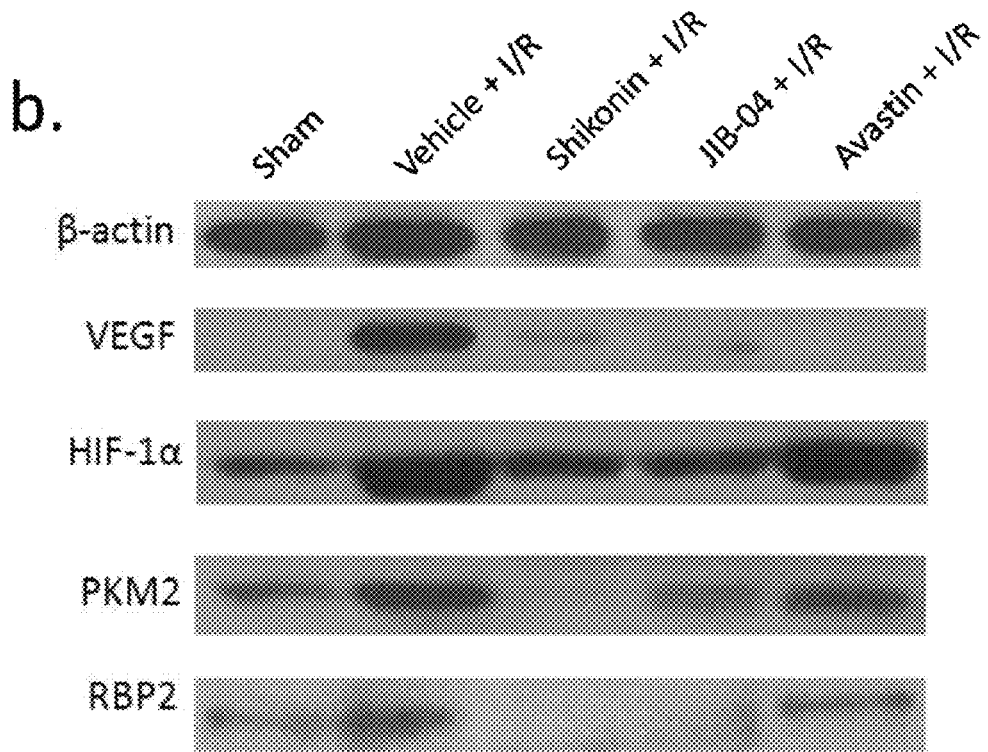
FIG. 8B shows the ratios of the protein expression levels of VEGF, HIF-1α, PKM2 or RBP2 relative to that of β-Actin. This figure shows the western blotting for expressions of β-Actin, VEGF, HIF-1α, PKM2 and RBP2. Lane 1 is from a control sham retina (Sham); Lane 2 is the vehicle-pretreated ischemic retina (Vehicle+I/R); Lane 3~5 are from retinas that received ischemia plus reperfusion and were preadministrated with 4 μM Shikonin (PKM2 inhibitor), 10 μM JIB-04 (RBP2 inhibitor) and 100 mg/4 ml Avastin (Anti-VEGF). VEGF: vascular endothelial growth factor, HIF-1α: hypoxia inducible factor 1α, PKM2: pyruvate kinase M2, RBP2: retinoblastoma-binding protein 2.
Figure 8C:
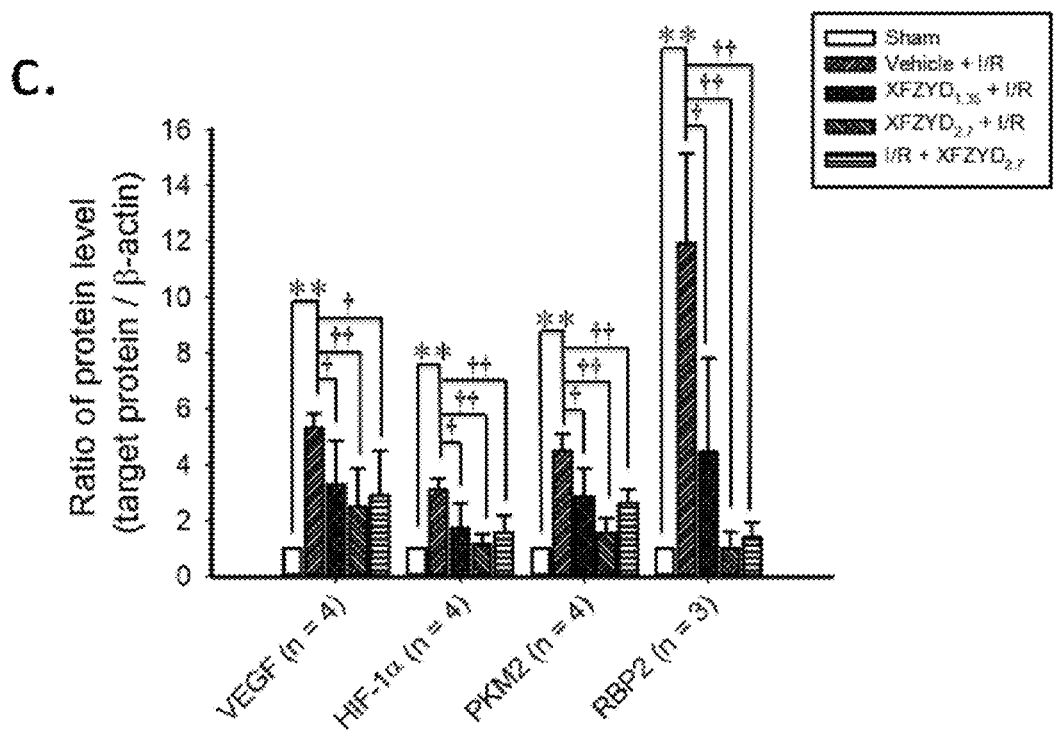
FIG. 8C shows the ratios of the protein expression levels of VEGF, HIF-1α, PKM2 or RBP2 relative to that of β-Actin. This picture shows the ratios of the protein expression levels of VEGF (n=4), HIF-1α (n=4), PKM2 (n=4) or RBP2 (n=3) relative to that of β-Actin. */** or †/†† represents significance (p<0.05/p<0.01; Sham vs. Vehicle+I/R) or significance (p<0.05/p<0.01; Vehicle+I/R vs. XFZYD$_{1.35}$+I/R, XFZYD$_{2.7}$+I/R, or I/R+XFZYD$_{2.7}$), respectively. Each bar indicates the mean±SD. VEGF: vascular endothelial growth factor, HIF-1α: hypoxia inducible factor 1α, PKM2: pyruvate kinase M2, RBP2: retinoblastoma-binding protein 2.
Figure 8D:
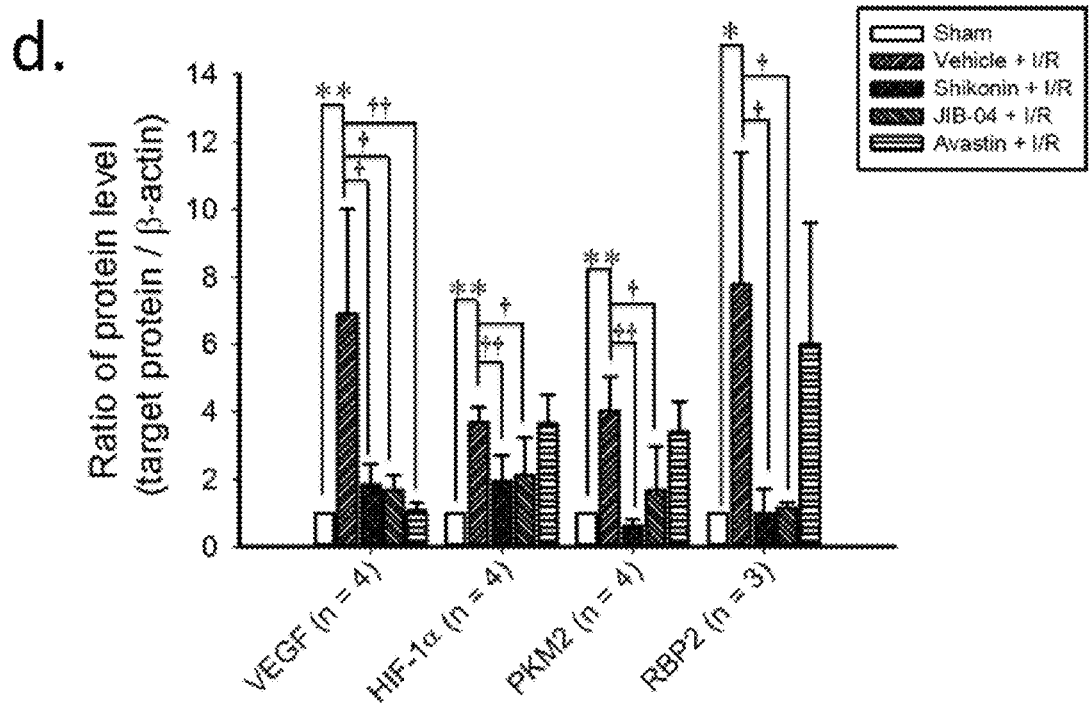
FIG. 8D shows the ratios of the protein expression levels of VEGF, HIF-1α, PKM2 or RBP2 relative to that of β-Actin. This figure shows the ratios of the protein expression levels of VEGF (n=4), HIF-1α (n=4), PKM2 (n=4) or RBP2 (n=3) relative to that of β-Actin. */** or †/†† represents significance (p<0.05/p<0.01; Sham vs. Vehicle+I/R) or significance (p<0.05/p<0.01; Vehicle+I/R vs. Shikonin+I/R, JIB-04+I/R, or Avastin+I/R), respectively. Each bar indicates the mean±SD. VEGF: vascular endothelial growth factor, HIF-1α: hypoxia inducible factor 1α, PKM2: pyruvate kinase M2, RBP2: retinoblastoma-binding protein 2.

As shown in FIGS. 8A and 8C (n=4 for VEGF, HIF-1α and PKM2; n=3 for RBP2), in contrast with the control retina (Sham; VEGF, HIF-1α, PKM2 and RBP2=1.00), after I/R and pre-ischemia administration of vehicle (VEGF=5.31±0.53, HIF-1α=3.10±0.40, PKM2=4.51±0.60, RBP2=11.92±3.22), there was a significant (n=4, VEGF, HIF-1α and PKM2, $p<0.001$; n=3, RBP2, $p=0.004$) increase in the ratios for VEGF, HIF-1α, PKM2 and RBP2. Moreover, this increase was in a dose-responsive manner (with a less effect at 1.35 g/kg/day) and significantly [$XFZYD_{1.35}$+I/R (VEGF=3.31±1.54, p=0.049; HIF-1α=1.71±0.92, p=0.032; PKM2=2.88±0.98, p=0.022; RBP2=4.46±3.35, p=0.049; $XFZYD_{2.7}$+I/R (VEGF=2.52±1.35, p=0.008; HIF-1α=1.16±0.36, PKM2=1.56±0.53, $p<0.001$; RBP2=1.00±0.59, p=0.004)] attenuated when ischemic retinas were preadministrated with 1.35 and 2.7 g/Kg/day of XFZYD. Post-ischemia administration of 2.7 g/Kg/day of XFZYD also significantly (I/R+$XFZYD_{2.7}$: VEGF=2.91±1.59, p=0.029; HIF-1α=1.57±0.61, p=0.006; PKM2=2.62±0.49, p=0.002; RBP2=1.42±0.52, p=0.005) attenuated this ischemia-induced increase. In addition (FIGS. 8B and 8D), significant attenuation of the ischemia-induced increase in the ratio for VEGF (Vehicle=6.92±1.55; Shikonin=1.84±0.60, p=0.018; JIB-04=1.68±0.46, p=0.016; Avastin=1.08±0.23, p=0.01), HIF-1α (Vehicle=3.69±0.22; Shikonin=1.95±0.76, p=0.007; JIB-04=2.14±1.11, p=0.04; Avastin=3.65±0.84, p=0.942), PKM2 (Vehicle=4.04±0.50; Shikonin=0.61±0.19, $p<0.001$; JIB-04=1.67±1.31, p=0.028; Avastin=3.42±0.88, p=0.390), and RBP2 (Vehicle=7.77±2.27; Shikonin=1.00±0.71, p=0.043; JIB-04=1.16±0.14, p=0.044; Avastin=6.00±3.61, p=0.597) was significantly attenuated, but not by vehicle, by pre-ischemia administration of the respective inhibitor/antibody 4 μM Shikonin (PKM2 inhibitor), 10 μM JIB-04 (RBP2 inhibitor) and 100 mg/4 ml Avastin (VEGF antibody). On the other hand, when the retinal protein levels of VEGF, HIF-1α, PKM2 and RBP2 were compared, no significant difference existed between the sham eye and the normal eye (n=4; VEGF=0.94±0.01, p=0.46; HIF-1α=0.92±0.02, p=0.26; PKM2=0.46±0.01, p=0.10; RBP2=1.22±0.09, p=0.37).

The data described above were expressed as the mean±standard deviation (SD). One-way analysis of variance (ANOVA) followed by Dunnett's test was performed for the comparison of the results in various groups (n=3~9). A p value of $<0.05$ was defined as statistically significant. Sigma Plot 12.5 (Systat Software, CA, USA) was used to carry out the analysis and plotting of graphs.

While the invention has been described and exemplified in sufficient detail for those skilled in this art to make and use it, various alternatives, modifications, and improvements should be apparent without departing from the spirit and scope of the invention.

One skilled in the art readily appreciates that the present invention is well adapted to carry out the objects and obtain the ends and advantages mentioned, as well as those inherent therein. The cells, animals, and processes and methods for producing them are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

The invention claimed is:

1. A method of preventing or treating a disease, disorder or condition induced by retina ischemia, comprising administrating to a subject a therapeutically effective amount of medicinal composition, wherein the composition comprising: 4.5 units by weight of Dang Gui, 1.5 units by weight of Chai Hu, 4.5 units by weight of Hong Hua, 3 units by weight of Zhi Qiao, 4.5 units by weight of Niu Xi, 1.5 units by weight of Gan Cao, from 2.25 to 2.3 units by weight of Chuan Xiong, 3 units by weight of Chi Shao, from 2.25 to 2.3 units by weight of Jie Geng, 6 units by weight of Táo Rén, and 4.5 units by weight of Di Huang.

2. The method according to claim 1, wherein the Chuan Xiong is 2.3 units by weights, and the Jie Geng is 2.3 units by weight.

3. The method according to claim 1, wherein said composition is in a form selected from the group consisting of a solution, a dispersion in liquid phases, a suspension, an emulsion, a granulate, a powder, a capsule, a tablet, a pill, a pellet, or a solid mixture.

4. The method according to claim 1, wherein the disease, disorder or condition is central retinal artery occlusion (CRAO), central retinal vein occlusion (CRVO), branch retinal artery occlusion (BRAO), branch retinal vein occlusion (BRVO), glaucoma, proliferative diabetic retinopathy (DR) or age-related macular degeneration (AMD).

5. The method according to claim 1, wherein the preventing or treating retinal ischemia is by downregulation of HIF-1α expression or VEGF secretion or both at the same time.

6. The method according to claim 5, wherein the downregulation of HIF-1α expression or VEGF secretion or both at the same time is by inhibition of RBP2 or PKM2 or both at the same time.

* * * * *